US010409052B2

(12) United States Patent
Liu et al.

(10) Patent No.: US 10,409,052 B2
(45) Date of Patent: Sep. 10, 2019

(54) INVERTED LIGHT-SHEET MICROSCOPE

(71) Applicant: University of Washington, Seattle, WA (US)

(72) Inventors: Jonathan T. Liu, Seattle, WA (US); Adam Glaser, Seattle, WA (US); Nicholas Reder, Seattle, WA (US); Lawrence D. True, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/719,299

(22) Filed: Sep. 28, 2017

(65) Prior Publication Data

US 2018/0088308 A1 Mar. 29, 2018

Related U.S. Application Data

(60) Provisional application No. 62/400,910, filed on Sep. 28, 2016.

(51) Int. Cl.
*G02B 21/36* (2006.01)
*G02B 21/26* (2006.01)
(Continued)

(52) U.S. Cl.
CPC ............ *G02B 21/367* (2013.01); *A61B 90/20* (2016.02); *G02B 21/26* (2013.01); *G02B 21/33* (2013.01);
(Continued)

(58) Field of Classification Search
CPC ........... G01N 21/6558; G01N 21/0303; G01N 21/553; G01B 9/21; G02B 21/16;
(Continued)

(56) References Cited

U.S. PATENT DOCUMENTS 7,706,060 B2 * 4/2010 Mogami ............ G01N 21/6458
359/385
7,880,891 B1 * 2/2011 Kim ...................... G01B 9/021
356/457
(Continued)

FOREIGN PATENT DOCUMENTS

WO 2015184124 12/2015
WO 2016054474 4/2016

OTHER PUBLICATIONS

Reder et al.; Light-Sheet Microscope Commercialization; Meeting Notes; Jun. 20, 2017; 21 pgs; University of Washington.
(Continued)

*Primary Examiner* — Tung T Vo
(74) *Attorney, Agent, or Firm* — Dorsey & Whitney LLP

(57) ABSTRACT

Devices and techniques for a light sheet microscope device are generally described. In some examples, the light sheet microscope may comprise a motorized movable stage comprising an optically clear glass plate. In some further examples, the light sheet microscope may comprise an illumination objective and a collection objective disposed on a first side of the optically clear glass plate. In some further examples, the light sheet microscope may comprise a wavefront- and index-matching element disposed on the first side of the optically clear glass plate. An oil layer may be disposed between the optically clear glass plate and the wavefront- and index-matching element. The oil layer, the wavefront- and index-matching element and the glass plate may have matching refractive indexes.

20 Claims, 17 Drawing Sheets

(51) Int. Cl.
  *G02B 21/33* (2006.01)
  *H04N 5/265* (2006.01)
  *H04N 5/374* (2011.01)
  *A61B 90/20* (2016.01)
  *H04N 5/225* (2006.01)
  *G02B 21/00* (2006.01)

(52) U.S. Cl.
  CPC ........... *H04N 5/2256* (2013.01); *H04N 5/265* (2013.01); *H04N 5/374* (2013.01); *G02B 21/0076* (2013.01); *H04N 2005/2255* (2013.01)

(58) Field of Classification Search
  CPC .. G02B 21/0032; G02B 21/367; G02B 21/26; G02B 21/33; G02B 21/0076; H04N 5/265; H04N 5/374; H04N 5/2256; A61B 90/20
  USPC .......................................................... 348/46
  See application file for complete search history.

(56) References Cited

U.S. PATENT DOCUMENTS

| | | | |
|---|---|---|---|
| 8,570,649 B2 | 10/2013 | Truong et al. | |
| 8,718,351 B2 | 5/2014 | So et al. | |
| 9,804,378 B2 | 10/2017 | Singer et al. | |
| 2001/0002315 A1* | 5/2001 | Schultz .................. | B82Y 30/00 436/172 |
| 2009/0074988 A1* | 3/2009 | Faris ....................... | B01J 19/00 427/596 |
| 2009/0147252 A1* | 6/2009 | Goto .................... | G01N 21/6458 356/244 |
| 2012/0135410 A1* | 5/2012 | Soni .................... | G01N 21/0303 435/6.12 |
| 2012/0243080 A1 | 9/2012 | Hattori et al. | |
| 2014/0320601 A1* | 10/2014 | Cutrale .................. | G02B 21/16 348/46 |
| 2015/0014540 A1* | 1/2015 | Ikushima ................ | G02B 13/14 250/340 |
| 2016/0299069 A1* | 10/2016 | Tao ....................... | G01N 21/553 |
| 2017/0052356 A1* | 2/2017 | Lei ...................... | G02B 21/0032 |

OTHER PUBLICATIONS

Siedentopf et al.; Uber Sichtbarmachung und Groben-bestimmung ultramikroskopischer Teilchen, mit besonderer Anwendung auf Goldrubinglaser (About Visualization and Gross Determination of Ultra-microscopic Particles, with Particular Application to Gold Rubbing Lasers); Annalen Der Physik; 1903; 40 pgs; 42277; No. 1; Leipzig.

Schmid et al.; An Abbreviated Standard Procedure for Accurate Tumor Volume Estimation in Prostate Cancer; The American Journal of Surgical Pathology; Feb. 1992; pp. 184-191; vol. 16; No. 2.

Hall et al.; Evaluation of Radical Prostatectomy Specimens; The American Journal of Surgical Pathology; Apr. 1992; pp. 315-324; vol. 16; No. 4.

Stelzer et al.; Fundamental Reduction of the Observation Volume in Far-field Light Microscopy by Detection Orthogonal to the Illumination Axis: Confocal Theta Microscopy; Optics Communications; Oct. 15, 1994; pp. 536-547; vol. 111.

True; Surgical Pathology Examination of the Prostate Gland; American Journal of Clinical Pathology; Nov. 1994; pp. 572-579; Special Article.

Stelzer et al.; A New Tool for the Observation of Embryos and Other Large Specimens: Confocal Theta Fluorescence Microscopy; Journal of Microscopy; Jul. 1995; 10 pgs; vol. 179.

Kino; Applications and Theory of the Solid Immersion Lens; Proceedings of SPIE; Jun. 23, 1999; 12 pages; Optoelectronics '99.

Hollenbeck et al.; Whole Mounted Radical Prostatectomy Specimens do not Increase Detection of Adverse Pathological Features; The Journal of Urology, Nov. 2000; pp. 1583-1586; vol. 164.

Smith Sehdev et al.; Comparative Analysis of Sampling Methods for Grossing Radical Prostatectomy Specimens Performed for Nonpalpable (Stage T1c) Prostatic Adenocarcinoma; Departments of Pathology, The Johns Hopkins Medical Institutions; May 2001; pp. 494-499; Baltimore, MD.

Singletary et al.; Revision of the American Joint Committee on Cancer Staging System for Breast Cancer; Journal of Clinical Oncology; Sep. 1, 2002; pp. 3628-3636; vol. 20; No. 17.

Bedossa et al.; Sampling Variability of Liver Fibrosis in Chronic Hepatitis C; Hepatology; Dec. 2003; pp. 1449-1457; vol. 38; No. 6.

Eichelberger et al.; Does pT2b Prostate Carcinoma Exist? Critical Appraisal of the 2002 TNM Classification of Prostate Carcinoma; Cancer; Apr. 28, 2004; pp. 2573-2576; vol. 100; No. 12.

Huisken et al.; Optical Sectioning Deep Inside Live Embryos by Selective Plane Illumination Microscopy; Science; Aug. 13, 2004; pp. 1007-1010; vol. 305.

Meyer et al.; Breast Carcinoma Malignancy Grading by Bloom-Richardson System vs Proliferation Index: Reproducibility of Grade and Advantages of Proliferation Index; Modern Pathology; May 13, 2005; pp. 1067-1078; vol. 18.

Srigley; Key Issues in Handling and Reporting Radical Prostatectomy Specimens; Archives of Pathology and Laboratory Medicine; Mar. 2006; pp. 303-317; vol. 130.

Liu et al.; Dual-axes Confocal Reflectance Microscope for Distinguishing Colonic Neoplasia; Journal of Biomedical Optics; Oct. 24, 2006; 10 pgs; vol. 11; No. 5.

Cabioglu et al.; Role for Intraoperative Margin Assessment in Patients Undergoing Breast-Conserving Surgery; Annals of Surgical Oncology; Jan. 28, 2007; pp. 1458-1471; vol. 14; No. 4.

Dodt et al.; Ultramicroscopy: Three-dimensional Visualization of Neuronal Networks in the Whole Mouse Brain; Nature Methods; Mar. 25, 2007; pp. 331-336; vol. 4; No. 4.

Zysk et al; Optical Coherence Tomography: A Review of Clinical Development from Bench to Bedside; Journal of Biomedical Optics; Oct. 24, 2007; 21 pgs; vol. 12; No. 5.

Roehrborn; Pathology of Benign Prostatic Hyperplasia; International Journal of Impotence Research; 2008; 8 pgs.

Waljee et al.; Predictors of Re-excision among Women Undergoing Breast-Conserving Surgery for Cancer; Annals of Surgical Oncology; Feb. 8, 2008; pp. 1297-1303; vol. 15; No. 5.

Jacobs; Positive Margins: The Challenge Continues for Breast Surgeons; Annals of Surgical Oncology; Mar. 5, 2008; pp. 1271-1272; vol. 15; No. 5.

Liu et al.; Efficient Rejection of Scattered Light Enables Deep Optical Sectioning in Turbid Media with Low-numerical-aperture Optics in a Dual-axis Confocal Architecture; Journal of Biomedical Optics; Jun. 11, 2008; 11 pgs; vol. 13; No. 3.

Aguet et al.; Model-based 2.5-D Deconvolution for Extended Depth of Field in Brightfield Microscopy; IEEE Transactions on Image Processing; Jul. 2008; pp. 1144-1153; vol. 17; No. 7.

Reynaud et al.; Light Sheet-based Fluorescence Microscopy: More Dimensions, More Photons, and Less Photodamage; HFSP Journal; Sep. 15, 2008; vol. 2; No. 5.

Gareau et al.; Confocal Mosaicing Microscopy in Mohs Skin Excisions: Feasibility of Rapid Surgical Pathology; Journal of Biomedical Optics; Sep. 22, 2008; 12 pgs; vol. 13; No. 5.

Keller et al.; Reconstruction of Zebrafish Early Embryonic Development by Scanned Light Sheet Microscopy; Science; Nov. 14, 2008; pp. 1065-1069; vol. 322.

Preibisch et al.; Globally Optimal Stitching of Tiled 3D Microscopic Image Acquisitions; Bioinformatics Applications Note; Apr. 3, 2009; pp. 1463-1465; vol. 25; No. 11.

Münch et al.: Stripe and Ring Artifact Removal with Combined Wavelet—Fourier Filtering; Optics Express; May 6, 2009; 25 pgs; vol. 17, No. 10.

Vakoc et al.; Three-dimensional Microscopy of the Tumor Microenvironment in vivo Using Optical Frequency Domain Imaging; Nature Medicine; Sep. 13, 2009; pp. 1219-1223; vol. 15; No. 10.

(56) References Cited

OTHER PUBLICATIONS

Gareau et al.; Line-scanning Reflectance Confocal Microscopy of Human Skin: Comparison of Full-pupil and Divided-pupil Configurations; Optics Letters; Oct. 15, 2009; pp. 3235-3237; vol. 34; No. 20.

Keller et al.; Fast, High-contrast Imaging of Animal Development with Scanned Light Sheet-based Structured-illumination Microscopy; Nature Methods; Jul. 4, 2010; pp. 637-645; vol. 7; No. 8.

Fahrbach et al.; A Line Scanned Light-sheet Microscope with Phase Shaped Self-reconstructing Beams; Optics Express; Nov. 4, 2010; 16 pgs; vol. 18; No. 23.

Santi; Light Sheet Fluorescence Microscopy: A Review; Journal of Histochemistry & Cytochemistry; Nov. 14, 2010; pp. 129-138; vol. 59; No. 2.

Planchon et al.; Rapid Three-dimensional Isotropic Imaging of Living Cells Using Bessel Beam Plane Illumination; Nature Methods; Mar. 4, 2011; pp. 417-426; vol. 8; No. 5.

Abeytunge; Rapid Confocal Imaging of Large Areas of Excised Tissue with Strip Mosaicing; Journal of Biomedical Optics; May 26, 2011; 4 pgs; vol. 16; No. 5.

Bini et al.; Confocal Mosaicing Microscopy of Human Skin ex vivo: Spectral Analysis for Digital Staining to Simulate Histology-like Appearance; Journal of Biomedical Optics; Jul. 14, 2011; 9 pgs; vol. 16; No. 7.

Truong et al.; Deep and Fast Live Imaging with Two-photon Scanned Light-sheet Microscopy; Nature Methods; Jul. 17, 2011; pp. 757-762; vol. 8; No. 9.

McKenney et al.: The Potential Impact of Reproducibility of Gleason Grading in Men with Early Stage Prostate Cancer Managed by Active Surveillance: A Multi-institutional Study; The Journal of Urology; Aug. 2011, pp. 465-469; vol. 186.

Mertz: Optical Sectioning Microscopy with Planar or Structured Illumination; Nature Methods; Sep. 29, 2011; pp. 811-819; vol. 8; No. 10.

Weber et al.; Light Sheet Microscopy for Real-time Developmental Biology; Science Direct, Current Opinion in Genetics & Development; Sep. 30, 2011; pp. 566-572; vol. 21.

Keller et al.; Digital Scanned Laser Light-sheet Fluorescence Microscopy (DSLM) of Zebrafish and *Drosophila* Embryonic Development; Imaging in Developmental Biology; Oct. 2011; pp. 1235-1244.

Cella Zanacchi; Live-cell 3D Super-resolution Imaging in Thick Biological Samples; Nature Methods; Oct. 9, 2011; pp. 1047-1049; vol. 8; No. 12.

Wu et al.; Inverted Selective Plane Illumination Microscopy (iSPIM) Enables Coupled Cell Identity Lineaging and Neurodevelopmental Imaging in Caenorhabditis Elegans; Proceedings of the National Academy of Sciences; Oct. 25, 2011; pp. 17708-17713; vol. 108; No. 43.

Fahrbach et al.; Propagation Stability of Self-reconstructing Bessel Beams Enables Contrast-enhanced Imaging in Thick Media; Nature Communications; Jan. 17, 2012; 8 pgs; vol. 3; No. 632.

Roberts et al; Toward Routine Use of 3D Histopathology as a Research Tool; American Journal of Pathology; May 5, 2012; pp. 1835-1842; vol. 180; No. 5.

Tomer et al.; Quantitative High-speed Imaging of Entire Developing Embryos with Simultaneous Multiview Light-sheet Microscopy; Nature Methods; Jun. 3, 2012; 14 pgs; vol. 9; No. 7.

Jeevan et al.; Reoperation Rates After Breast Conserving Surgery for Breast Cancer among Women in England: Retrospective Study of Hospital Episode Statistics; Biomedical Journal; Jul. 12, 2012; 9 pgs.

Tarjan et al.; Improved Differentiation between Ductal and Acinar Prostate Cancer using Three-dimensional Histology and Biomarkers; Scandinavian Journal of Urology and Nephrology; Aug. 2012; pp. 258-266; vol. 46.

Mei et al.; A Line Scanning Confocal Fluorescent Microscope Using a CMOS Rolling Shutter as an Adjustable Aperture; Journal of Microscopy; Aug. 20, 2012; pp. 269-276; vol. 247.

Carlson et al.; A Primer on the Cost of Quality for Improvement of Laboratory and Pathology Specimen Processes; Anatomic Pathology; American Society for Clinical Pathology; Sep. 2012; pp. 347-354; vol. 138.

Bolenz et al.; Costs of Radical Prostatectomy for Prostate Cancer: A Systematic Review; European Urology; Sep. 4, 2012; pp. 316-324.

Baumgart et al.; Scanned Light Sheet Microscopy with Confocal Slit Detection; Optics Express; Sep. 7, 2012; pp. 21805-21814; vol. 20; No. 19.

Barakat et al.; Reliability of Frozen Section in Breast Sentinel Lymph Node Examination; Breast Cancer; Nov. 29, 2012; pp. 576-582; The Japanese Breast Cancer Society; Original Article.

Abeytunge et al.; Confocal Microscopy with Strip Mosaicing for Rapid Imaging over Large Areas of Excised Tissue; Journal of Biomedical Optics; Feb. 6, 2013; 14 pgs; vol. 18; No. 6.

Tejeda et al.; Comparison between Bessel and Gaussian Beam Propagation for in-depth Optogenetic Stimulation; Proceedings of SPIE; Mar. 8, 2013; 8 pgs.

Fahrbach et al.; Self-reconstruction Sectioned Bessel Beams Offer Submicron Optical Sectioning for Large Fields of view in Light-sheet Microscopy; Optics Express; May 2, 2013; pp. 11425-11440; vol. 21; No. 9.

Chung et al.; Structural and Molecular Interrogation of Intact Biological Systems; Nature; May 16, 2013; pp. 332-337; vol. 497.

Adams et al.; The Role of Margin Status and Reexision in Local Recurrence Following Breast Conservation Surgery; Annals of Surgical Oncology; May 18, 2013; pp. 2250-2255.

Fahrbach et al.; Light-sheet Microscopy in Thick Media using Scanned Bessel Beams and Two-photon Fluorscence Excitation; Optics Express; May 31, 2013; pp. 13824-13839; vol. 21; No. 11.

Pitrone et al.; OpenSPIM: an Open-access Light-sheet Microscopy Platform; Nature Methods; Jun. 9, 2013; pp. 598-599; vol. 10; No. 7.

Schlichenmeyer et al.; Video-rate Structured Illumination Microscopy for High-throughput Imaging of Large Tissue Areas; Biomedical Optics Express; Jan. 7, 2014; pp. 366-377; vol. 5; No. 2.

Author unknown; Depth of Field and Depth of Focus; The Imaging Resource Guide; Mar. 14, 2014; Section 4.4; 11 pgs; downloaded from: https://www.edmundoptics.com/resources/application-notes/imaging/depth-of-field-and-depth-of-focus/ on Jul. 31, 2018.

Vettenburg et al.; Light-sheet Microscopy using an Airy Beam; Nature Methods; Apr. 6, 2014; pp. 541-544; vol. 11; No. 5.

Moran et al.; Society of Surgical Oncology—American Society for Radiation Oncology Consensus Guideline on Margins for Breast-Conserving Surgery with Whole-Breast Irradiation in Stages I and II Invasive Breast Cancer; Journal of Clinical Oncology; May 10, 2014; pp. 1507-1515; vol. 32; No. 14.

Wang et al.; Sheet-scanned Dual-axis Confocal Microscopy Using Richardson-Lucy Deconvolution; Optics Letters; Sep. 15, 2014; pp. 5431-5434; vol. 39; No. 18.

Kumar et al.; Dual-view Plane Illumination Microscopy for Rapid and spatially Isotropic Imaging; Nature Protocols; Oct. 9, 2014; pp. 2555-2573; vol. 9; No. 9.

Assayag et al.; Large Field, High Resolution Full-Field Optical Coherence Tomography: A Pre-clinical Study of Human Breast Tissue and Cancer Assessment; Technology in Cancer Research and Treatment; Oct. 2014; pp. 455-468; vol. 13; No. 5.

Tao et al.; Assessment of Breast Pathologies Using Nonlinear Microscopy; Proceedings of the National Association of Sciences; Oct. 28, 2014; pp. 15304-15309; vol. 111; No. 43.

Reynaud et al.; Guide to Light-sheet Microscopy for Adventurous Biologists; Nature Methods; Jan. 2015; pp. 30-34; vol. 12; No. 1.

Bouchard et al.; Swept Confocally-aligned Planar Excitation (SCAPE) Microscopy for High-speed Volumetric Imaging of Behaving Organisms; Nature Photonics; Jan. 19, 2015; pp. 113-119; vol. 9.

Pampaloni et al.; Light Sheet-based Flourescence Microscopy (LSFM) for the Quantitative Imaging of Cells and Tissues; Cell and Tissue Research; Mar. 6, 2015; pp. 129-141.

Fereidouni et al.; Microscopy with UV Surface Excitation (MUSE) for Slide-free Histology and Pathology Imaging; Proceedings of SPIE; Mar. 11, 2015; 7 pgs.

(56) References Cited

OTHER PUBLICATIONS

Yang et al.; Dual-slit Confocal Light Sheet Microscopy for in vivo Whole-brain Imaging of Zebrafish; Biomedical Optics Express; Apr. 21, 2015; pp. 1797-1811; vol. 6; No. 5.
Yang et al.; Rapid Imaging of Large Tissues Using High-resolution Stage-Scanning Microscopy; Biomedical Optics Express; Apr. 23, 2015; pp. 1867-1875; vol. 6; No. 5.
McGorty et al.; Open-top Selective Plane Illumination Microscope for Conventionally Mounted Specimens; Optics Express; Jun. 9, 2015; 12 pgs; vol. 23; No. 12.
Jonkman et al.; Any Way You Slice it—a Comparison of Confocal Microscopy Techniques; Journal of Biomolecular Techniques; Jul. 2015; pp. 54-65; vol. 26; No. 2.
Richardson et al.; Clarifying Tissue Clearing; Leading Edge Review; Jul. 16, 2015; pp. 246-257.
Wang et al.; High-resolution Rapid Diagnostic Imaging of Whole Prostate Biopsies using Video-rate Fluorescence Structured Illumination Microscopy; Cancer Research; Aug. 17, 2015; pp. 4032-4042; vol. 75; No. 19.
Shah et al.; Diagnosis of Gleason Pattern 5 Prostate Adenocarcinoma on Core Needle Biopsy; American Journal of Surgical Pathology; Sep. 2015; pp. 1242-1249; vol. 39; No. 9.
Zhou et al.; Diagnosis of "Poorly Formed Glands" Gleason Pattern 4 Prostatic Adenocarcinoma on Needle Biopsy; American Journal of Surgical Pathology; Oct. 2015; pp. 1331-1339; vol. 39; No. 10.
Medeiros et al.; Confocal Multivew Light-sheet Microscopy; Nature Communications; Nov. 25, 2015; 8 pgs.
Strnad et al.; Inverted Light-sheet Microscope for Imaging Mouse Pre-implantation Development; Nature Methods; Dec. 14, 2015; pp. 139-145; vol. 13; No. 2.
Glaser et al; A Light-Sheet Microscopy System for Rapid, Volumetric Imaging and Pathology of Large Tissue Specimens; Biomedical Optics Congress 2016; 2016; 3 pgs.
Glaser et al; Assessing the Imaging Performance of Light Sheet Microscopies in Highly Scattering Tissues; Biomedical Optics Express; Jan. 14, 2016; vol. 7; No. 2.
Bria et al.; TeraFly: Real-time Three-dimensional Visualization and Annotation of Terabytes of Multidimensional Volumetric Images; Nature Methods; Mar. 2016; pp. 192-194; vol. 13; No. 3.
Giacomelli et al.; Design of a Portable Wide Field of View GPU-accelerated Multiphoton Imaging System for Real-time Imaging of Breast Surgical Specimens; Proceedings of SPIE; Mar. 14, 2016; 7 pgs.
Fu et al.; Imaging Multicellular Specimens with Real-time Optimized Tiling Light-Sheet Selective Plane Illumination Microscopy; Nature Communications; Mar. 23, 2016; 10 pgs.
Lavagnino et al.; 4D (x-y-z-t) Imaging of Thick Biological Samples by Means of Two-photon Inverted Selective Plane Illumination Microscopy (2PE-iSPIM); Scientific Reports; Apr. 1, 2016; 9 pgs.
Tu et al.; Stain-free Histopathology by Programmable Supercontinuum Pulses; Nature Photonics; May 23, 2016; pp. 534-541; vol. 10.
Yang et al.; An Inverted Light Sheet Microscope Optimized for Studies in Neuroscience; 2016 Conference on Lasers and Electro-Optics; Optical Society of America; Jun. 2016; 2 pgs.
Wang et al.; Gigapixel Surface Imaging of Radical Prostatectomy Specimens for Comprehensive Detection of Cancer-Positive Surgical Margins Using Structured Illumination Microscopy; Scientific Reports; Jun. 3, 2016; 16 pgs.
Van Royen et al; Three-dimensional Microscopic Analysis of Clinical Prostate Specimens; Histopathology; Jun. 29, 2016; pp. 985-992; vol. 69.
Chen et al.; Nanoscale Imaging of RNA with Expansion Microscopy; Nature Methods; Jul. 4, 2016; pp. 679-687; vol. 13; No. 8.
Olsen et al.; Multiphoton Microscopy with Clearing for Three Dimensional Histology of Kidney Biopsies; Biomedical Express; Aug. 1, 2016; 8 pgs; vol. 7; No. 8.
Giacomelli et al.; Virtual Hematoxylin and Eosin Transillumination Microscopy Using Epi-fluorescence Imaging; The Public Library of Science; Aug. 8, 2016; 13 pgs.
Liu et al.; Bringing Clarity to the Human Brain: Visualization of Lewy Pathology in Three Dimensions; Neuropathology and Applied Neurobiology; Oct. 2016; pp. 573-587; vol. 42.
Elfer et al.; DRAQ5 and Eosin ('D&E') as an Analog to Hematoxylin and Eosin for Rapid Fluorescence Histology of Fresh Tissues; The Public Library of Science; Oct. 27, 2016; 18 pgs.
Moffitt et al.; High-performance Multiplexed Fluorescence in situ Hybridization in Culture and Tissue with Matrix Imprinting and Clearing; Proceedings of the National Academy of Sciences; Dec. 13, 2016; pp. 14456-14461; vol. 113; No. 50.
Tozbikian et al.; Atypical Ductal Hyperplasia Bordering on Ductal Carcinoma in situ: Interobserver Variability and Outcomes in 105 Cases; International Journal of Surgical Pathology; 2017; pp. 100-107; vol. 25; No. 2.
Orringer et al; Rapid Interoperative Histology of Unprocessed Surgical Specimens via Fibre-laser-based Stimulated Raman Scattering Microscopy; Nature Biomedical Engineering; Feb. 6, 2017; 13 pgs; vol. 1.
Dean et al.; Imaging Subcellular Dynamics with Fast and Light-efficient Volumetrically Parallelized Microscopy; Optica; Feb. 17, 2017; pp. 263-271; vol. 4; No. 2.
Power et al.; A Guide to Light Sheet Fluorescence Microscopy for Multiscale Imaging; Nature Methods; Mar. 31, 2017; pp. 360-373; vol. 14; No. 4.
Glaser et al.; Light-sheet Microscopy for Slide-free Non-destructive Pathology of Large Clinical Specimens; Nature Biomedical Engineering; Jun. 26, 2017; 10 pgs; vol. 1.
Davidson; Resolution; Basic Concepts and Formulas in Microscopy; Microscopy U; downloaded from https://www.microscopyu.com/microscopy-basics/resolution on Jul. 31, 2018.
Author unknown; Surveillance; Epidemiology and End Results Program; National Cancer Institute; downloaded from https://seer.cancer.gov/faststats/index.php on Sep. 1, 2018.
Reder et al.; Light-sheet Microscope Commercialization; Jun. 20, 2017; 21 pgs.
Computer-Generated Translation of Siedentopf et al.; Uber Sichtbarmachung und Groben-bestimmung ultramikroskopischer Teilchen, mit besonderer Anwendung auf Goldrubinglaser (About Visualization and Gross Determination of Ultra-microscopic Particles, with Particular Application to Gold Rubbing Lasers); 1903; retrieved from Google Patents on Dec. 12, 2018; 39 pgs.

\* cited by examiner

INVERTED LIGHT-SHEET MICROSCOPE

CROSS-REFERENCE TO RELATED APPLICATIONS

This application claims the benefit of U.S. Provisional Application No. 62/400,910, filed Sep. 28, 2016, the disclosure of which is incorporated herein by reference in its entirety.

STATEMENT OF GOVERNMENT LICENSE RIGHTS

This invention was made with government support under Grant Nos. CA175391 and DE023497, awarded by the National Institutes of Health (NIH). The government has certain rights in the invention.

FIELD

This application relates to imaging techniques and devices for use in pathology.

BACKGROUND

For microscopic inspection of fresh tissues obtained during or after surgical resection, or through a biopsy procedure, pathologists typically rely upon histology methods that require the tissues to be chemically fixed or frozen, embedded in wax or a freezing compound, sectioned, mounted, and stained on a glass slide. Various optical-sectioning microscopy methods are also used in pathology. Optical-sectioning microscopy provides a 2D image with a narrow depth of focus and often employs elaborate tissue-flattening and alignment procedures to image irregular surfaces of fresh tissue specimens. Additional challenges have included insufficient resolution, contrast, field of view, and/or imaging speed, all of which have limited the clinical viability of these prior systems.

SUMMARY

In various examples, systems and methods are provided for particle analysis devices including periodic dielectric structures.

A wide-area inverted light-sheet microscope (LSM) is described herein. The LSM allows for volumetric microscopy over an extended depth of focus with high resolution, two parameters that typically must trade off with traditional single-axis microscope configurations. By rapidly scanning a specimen to obtain a thin volumetric dataset, irregular tissue surfaces can be digitally extracted and visualized. LSM systems, as described herein, may image fresh tissue surfaces at high speed (<1 min/cm$^2$) over a wide-area (e.g., 10×10 cm) with high resolution (~2 μm or better) and contrast (a usable imaging depth in fresh uncleared tissues of ~50 μm and at a usable imaging depth in cleared tissues of ~500 μm or more).

Histopathology, the current gold standard for tissue diagnosis, is a laborious process that typically requires several days and is therefore not feasible for certain clinical scenarios (e.g., real-time guidance of surgical resections or biopsy procedures). For tumor-resection procedures, excised tissues are examined histologically after surgery to determine if the surgical margins are clean (without tumor) and also to assess the grade, location, size, and/or other features that may be used for risk stratification and to guide adjuvant therapies. For large excisions (e.g., up to several cm in size or larger), the fresh specimens are first manually sliced into thick cross sections (or "bread loafs") ranging from 0.3 to 1 cm in thickness (depending upon the organ). For permanent (archival) histopathology, these slices are then chemically fixed, dehydrated, and embedded in paraffin wax such that a few thin physical sections (~5 μm in thickness) may be cut from the surface of each tissue slice and mounted on glass microscope slides. The tissue sections are then stained, most often with hematoxylin and eosin ("H&E"), protected with a coverslip, and finally evaluated at the microscopic level by a pathologist. Despite the time-consuming nature of this workflow, histology of formalin-fixed paraffin-embedded ("FFPE") tissues has remained a largely unchanged clinical standard for over a century.

Frozen sections are a faster alternative to FFPE histology and are used for intraoperative guidance of certain surgical oncology procedures, such as skin-cancer resections (e.g., Mohs micrographic surgeries), where thin tissue sections are directly cut from tissues that are rapidly frozen, thereby avoiding the need for chemical fixation, dehydration, and paraffin embedding. However, these tissue sections must still undergo cryo-embedding, sectioning, staining, and slide mounting steps, such that at least 20 min is required for frozen sections to be prepared. Frozen sections exhibit more artifacts and provide poorer image quality compared to FFPE histology, and are therefore not relied upon for archival post-surgical pathology.

Both conventional FFPE and frozen-section histology suffer from severe sampling errors due to the fact that only a small fraction (typically <1%) of a tissue specimen can be sectioned into thin slide-mounted sections in a busy clinical pathology lab with limited reimbursement. For margin assessment, the sampling issue is further exacerbated by the fact that tissues are typically sectioned in the vertical direction (depth direction) in relation to the tissue surface, and only one edge of the thin tissue section corresponds to the surgical margin (i.e., the "inked" surface). En face sections are possible, in which the tissue is sectioned parallel to the tissue surface. However, it is extremely difficult to prepare an en face section from a plane that is within a distance of 10-20 μm of the tissue surface, especially for a large surface that is irregular (not flat). Even if the tissue can be flattened over small regions (and embedded in wax or freezing compound), another difficulty is in aligning a microtome or cryotome blade such that it slices the tissue precisely parallel to the flattened tissue surface.

Based on the limitations of current permanent and frozen histology methods, as discussed in the previous paragraphs, there is great interest in a means for rapid, wide-area, and high-quality (high resolution and contrast) microscopic inspection of the surfaces of freshly excised surgical specimens, and/or fresh tissue slices. Unlike conventional cross-sectional histopathology, there would be value in a device that could enable comprehensive sub-cellular-resolution imaging of unprocessed fresh tissue surfaces over extremely large areas (multiple cm$^2$ in surface area). In summary, a number of clinical scenarios would benefit from such a device. The following examples, which are by no means an exhaustive list of potential clinical applications, include:

1. Intra-Operative Guidance of Surgical Resections or Biopsy Procedures.

Currently, there is a need to assess excised tissues during tumor-resection or biopsy procedures in order to identify residual tumor at the surgical margins or to confirm that the biopsied tissue is adequate for downstream microscopic and/or molecular analyses (e.g. non-necrotic viable tumor).

For example, in breast-conserving surgery, 20-60% of patients must undergo additional surgery when post-operative pathology reveals tumor at or near the surgical margin, indicating an incomplete removal of the tumor mass. Such follow-up procedures are expensive/traumatic, risky due to potential for iatrogenic injury, and could be avoided with a rapid intraoperative pathology method.

2. Triaging of Normal Tissues to Accelerate Post-Operative Pathology.

Following certain surgical procedures, pathology labs must process prohibitively large volumes of tissue. Oftentimes, these large specimens cannot be adequately sampled due to healthcare-cost and labor constraints. For example, when an entire prostate is removed (radical prostatectomy), the organ is first bread loafed into 0.3- to 0.5-mm thick slices, where each slice is typically then cut into quarters due to the large surface area of each slice. As a result of this large volume of tissue, 90% of US labs employ partial sampling strategies, which are blind and simply consist of processing only half of the tissue slices. This results in sampling errors and inferior pathology quality (e.g. risk stratification), which may be prevented by a rapid wide-area surface microscopy method that would allow pathologists to accurately triage normal prostate slices and perform a full histological work up only on tissue slices containing malignancy.

To address these needs for fresh-tissue microscopy, a number of research groups have investigated various techniques such as confocal microscopy, nonlinear microscopy, structured-illumination microscopy (SIM), and wide-field microscopy with UV excitation (MUSE) to rapidly obtain high-quality wide-area pathologic images. Fluorescent dyes such as acridine orange, are able to rapidly highlight cell nuclei (in the case of acridine orange), or other microarchitectural features, with the ability to provide images comparable to H&E histology (if so desired). In contrast to physically sectioned tissues these microscopy methods provide optical-sectioning of thick tissues by rejecting out-of-focus and multiply scattered background light. In the case of confocal microscopy, optical-sectioning is achieved by using a physical pinhole to spatially filter out background light. Nonlinear microscopy relies upon localized generation of signal at the focus of an illumination beam (or beams) to suppress the generation of out-of-focus signal photons. In SIM, sectioning is achieved digitally by demodulating patterns of light that are projected onto the tissue surface, in which the spatial patterns are preferentially imaged with high contrast only within a thin illumination light sheet of the microscope, and thereby allows for signals from that focal plane to be distinguished from out-of-focus background signals. Finally, MUSE relies upon the extremely limited penetration depth of UV light in tissue, such that a high-contrast image of the tissue surface may be acquired with a detector array, with minimal background from below the tissue surface. Confocal and nonlinear microscopy techniques require scanning and therefore typically exhibit slow imaging speeds. SIM is known to produce poor image contrast in samples thicker than 50 μm due to limitations in detector dynamic range and shot noise from the background light that is not physically blocked from the detector. MUSE is limited to imaging the surface of a tissue, with no depth-imaging capability.

A significant practical shortcoming of previous microscopy techniques has been the use of a focused illumination and collection beam along a single-axis, which results in a narrow depth of focus (<5 μm) for the high numerical aperture (NA) necessary to provide nuclear resolution (1-2 μm). This is a consequence of the trade-off between spatial resolution and depth of focus, as dictated by diffraction theory, which constrains a single-axis microscope. A narrow depth of focus is a major practical impediment for the rapid imaging of freshly cut tissue specimens, where the presence of surface irregularities (on the order of a few hundred microns) are difficult to avoid and cause defocusing of the tissue surface throughout the imaged field of view. For example, prostate tissues containing benign prostatic hyperplasia (BPH) nodules can be particularly stiff and difficult to flatten for imaging purposes. Even if the tissue can be flattened, another technical challenge is aligning the tissue surface (specimen tilt) to be perfectly parallel to the focal plane of the microscope (i.e. <5 μm of deviation over a field of view of several cm). Although elaborate flattening and alignment techniques are possible to mitigate the effects of these surface irregularities and sample-tilt issues, they are logistically difficult and time-consuming for a pathologist to implement.

In accordance with some embodiments of the present invention, light sheet microscopes are generally described. In various examples, the light sheet microscopes may comprise a motorized movable stage comprising an optically clear plate. In some further examples, the light sheet microscopes may comprise an illumination objective disposed on a first side of the optically clear glass plate. In various additional examples, the light sheet microscopes may comprise a collection objective disposed on the first side of the optically clear glass plate. In some examples, the light sheet microscopes may further comprise a wavefront- and index-matching element disposed on the first side of the optically clear plate. In some examples, the light sheet microscopes may further comprise an oil layer disposed between the wavefront- and index-matching element and the optically clear plate. In various examples, the optically clear plate, the oil of the oil layer, and the wavefront- and index-matching element may comprise a first refractive index value. In some examples, an illumination beam of light may pass through the wavefront- and index-matching element, through the oil layer, through the optically clear plate and may form a illumination light sheet on a second side of the optically clear plate opposite the first side of the optically clear plate.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

In the following description, reference is made to the accompanying drawings that illustrate several embodiments of the present disclosure. It is to be understood that other embodiments may be utilized and system or process changes may be made without departing from the spirit and scope of the present disclosure. The following detailed description is not to be taken in a limiting sense, and the scope of the embodiments of the present invention is defined only by the claims of the issued patent. It is to be understood that drawings are not necessarily drawn to scale.

The various light sheet microscopy (LSM) systems described in the present disclosure may be effective to perform rapid, wide-area microscopy of fresh tissues with irregular surfaces. In LSM the illumination and collection paths are separated and oriented orthogonally to each other. Unlike conventional confocal and nonlinear microscopy (where the depth of focus is fundamentally limited), and SIM (where contrast and depth of focus are also limited), in certain implementations, LSM can achieve imaging over a large depth of focus by selectively illuminating a single plane within the tissue with a low-numerical aperture ("NA") light sheet. By directly imaging this two-dimensional (2D) light sheet onto a detector array, it is possible to achieve rapid, high-resolution, three-dimensional (3D) microscopy. In various examples, LSM may be used in the fields of developmental and cell biology to perform high-resolution, volumetric imaging on relatively transparent model organisms (e.g., *Drosophila*, embryos, and nematodes) that are embedded in agar or an aqueous solution.

In the context of imaging fresh surgical or biopsied specimens, an inverted LSM system is attractive in that it can rapidly provide in-focus images from a volumetric field of view. If an irregular tissue surface is contained within this volume, the surface may be digitally flattened (segmented out) such that large tissue surfaces may be visualized at high resolution. In addition, depth-resolved imaging of cell layers near the tissue surface is also possible. The various LSM systems described herein may provide high-contrast images to a usable depth of ~50 μm in fresh uncleared tissues (assuming a scattering coefficient, $\mu_s$ ~10 $mm^{-1}$), which is equivalent to ~10 physical histology sections. Providing high-contrast images to this depth is potentially of great significance for pathologists, as the 3D microstructure of a number of cancer types (e.g., prostate) has been shown to be of diagnostic value. Additionally, in various examples, cleared tissue and other cleared samples may be imaged to a depth of up to about ~500 μm.

Figure 1:
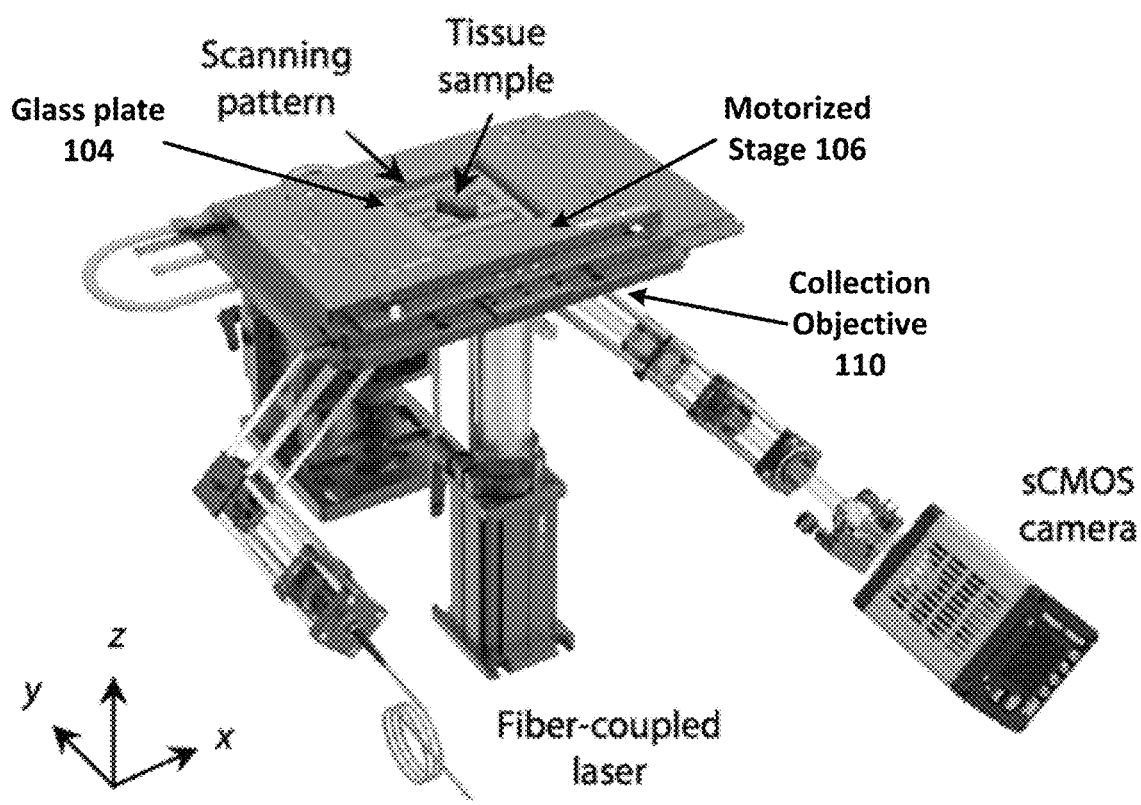
FIG. 1 depicts an example of a light sheet microscope device for rapid, wide-area, volumetric imaging of fresh tissues, in accordance with various aspects of the present disclosure.

FIG. 1 depicts an example of a light sheet microscope device 102 for rapid, wide-area, volumetric imaging of fresh tissues, in accordance with various aspects of the present disclosure. A novel sample interface was designed to allow for aberration-free imaging of these samples on a flat, optically clear glass plate 104 with oblique illumination and collection beams (angled at approximately 45 degrees (e.g., +/−1%) with respect to flat glass plate 104). In various examples, optically clear glass plate may be optically clear in the sense that it transmits the illumination light and collection light of LSM device 102. In conjunction with a motorized stage 106 and a scientific complimentary metal oxide semiconductor ("sCMOS") camera, the LSM device 102 may achieve high-speed imaging (<1 min/$cm^2$) over a wide-area (e.g., 10×10 cm) with high resolution (~2 μm or better) and contrast (to a usable imaging depth of ~50 μm in fresh uncleared tissues or samples and up to about 500 μm in cleared tissues or samples), without the need for elaborate system alignment and/or tissue-flattening.

LSM device 102 may comprise a glass plate 104 on the motorized stage 106. Glass plate 104 may comprise fused silica. Samples to be imaged may be placed on glass plate 104. LSM device 102 may comprise an illumination objective comprising illumination optics effective to generate a Gaussian-profile light sheet within a tissue sample placed on glass plate 104, as described in further detail below. LSM device 102 may comprise a low-power (1-100 mW) continuous-wave (CW) laser as an illumination source. In various examples, the laser may emit in free space or through a single mode optical fiber. Fluorescence from the tissue sample may be collected by a collection objective 110 comprising an objective lens, L2, (e.g., 4×NA=0.28). The combination of illumination and collection NA may provide sufficient contrast (e.g., signal-to-background ratio) to image most fresh uncleared tissues (or other samples) down to a depth of ~50 μm with subcellular lateral resolution of ~2.0 μm or better (depending upon the optics used). Additionally, the combination of illumination and collection NA may provide sufficient contrast to image cleared tissues or other samples to a depth of up to about 500 μm. Image data (e.g., frames of image data) may be collected by a complimentary metal oxide semiconductor image sensor, such as a scientific sCMOS image sensor with a desired sampling pitch (e.g. ~1 μm/pixel, which is Nyquist sampling for a system with 2-μm resolution). The image sensor and the collection objective may be configured in an optical alignment that allows the image sensor to image the 2D light sheet generated by the illumination path, as depicted in the example optical configuration shown in FIG. 9.

In contrast to conventional LSM systems that have been optimized for the imaging of relatively transparent samples that are embedded within a small imaging volume, the wide-area inverted LSM device 102 depicted in FIG. 1 may use a 45 degree "tilted or oblique" beam path that enables the bottom surface of thick fresh tissues to be imaged when placed on flat glass plate 104. In the LSM device 102, the illumination/collection optics (e.g., the illumination objective and collection objective 110) are disposed on a first side of flat glass plate 104 while the sample sits on the other side (e.g., the top side) of the flat glass plate 104. This "open-top" architecture may be advantageous as it frees the sample side (e.g., the top side) of the sample holder to accommodate samples of arbitrary size and shape, large petri dishes, multi-well plates, and/or microfluidic chips. Similarly, in the context of imaging fresh tissues, the open-top architecture allows for the imaging of thick samples, in which the bottom surface may be flattened (to some degree) against the flat glass plate 104. However, in at least some examples, this open-top geometry may introduce design challenges, as the highly off-axis (e.g., 45-degrees with respect to the flat glass plate 104) illumination objective and collection objective are not easily refraction index-matched into the sample through air or water-immersion, and, as a result, may suffer from significant aberrations.

The mitigation of optical aberrations may be critical to the success of LSM device 102, in which any aberration-correcting optical elements must be designed to not interfere with the mechanical scanning of the motorized stage 106 of the LSM device 102. Motorized stage 106 of LSM device 102 may be effective to position the optically clear glass plate (e.g., glass plate 104) at various positions in order to image a sample positioned on the optically clear glass plate. In some previous examples, a water-filled glass prism was used to mitigate optical aberrations. The prism faces minimized optical aberrations due to highly off-axis illumination and collection optics, and the water-filling enables stage-scanning. Unfortunately, the flat prism face does provide optimal aberration mitigation for the illumination and collection wave fronts, and the water evaporates over time. Instead, LSM device 102 may use a wavefront- and index-matching element 212 (depicted in FIG. 2) and index-matching oil layer 112 (depicted in FIG. 2) as an interface between the illumination and collection wave fronts and glass plate 104. In various examples, wavefront- and index-matching element 212 may be a wavefront-matching immersion lens having at least one curved surface effective to perform wavefront-matching and comprising a material that is index-matched with respect to oil of oil layer 112 and glass plate 104. In some examples, the wavefront- and index-matching element 212 may be a solid immersion lens (SIL) and/or a truncated hemispherical immersion lens. In some examples, the curvature of various surfaces of wavefront- and index-matching element 212 may be selected so that illumination and collection beams propagating through the curved surfaces are wavefront-matched and index-matched. Any shape may be used for portions of wavefront- and index-matching element 212 through which the illumination and collection beams do not propagate. In various examples, at least some exterior surfaces of the wavefront- and index-matching element 212 may comprise a spherical curvature, however the wavefront- and index-matching element 212 may also comprise aspherical surfaces. In some examples, the wavefront- and index-matching element 212 may comprise a number of constituent lenses combined to achieve index-matching and optical aberration mitigation. Additionally, in at least some examples, the wavefront- and index-matching element 212 may be combined with other optics to provide for index-matching and optical aberration mitigation. Further, in some examples, wavefront- and index-matching element 212 may be at least partially filled with an index-matching fluid to index match the illumination and collection wave fronts as they transition through the wavefront- and index-matching element 212. In various examples, wavefront- and index-matching element 212 may be a truncated hemispherical lens to optimize the performance of the wavefront- and index-matching element for beams that focus slightly past the flat distal surface of the wavefront- and index-matching element 212. In some examples, an aspheric curvature at the proximal end of the wavefront- and index-matching element 212 may be used to correct for optical aberrations. In various examples, wavefront- and index-matching element 212 may be fabricated with a gradient refractive index profile to allow the wavefront- and index-matching element to achieve higher performance relative to a homogeneous-index solid immersion lens at the edges of the field of view. Oil layer 112 allows for glass plate 104 to be translated by the motorized stage 106 while maintaining the positions of the illumination objective, the collection objective 110 and the wavefront- and index-matching element 212. LSM device 102 may be aligned such that the beam waist of the illumination light sheet 230 is positioned within about 1-200 microns or within about 50-150 microns above the glass plate 104. The illumination light sheet 230 may have a depth of focus (confocal parameter) of about 400 microns. Accordingly, the illumination light sheet 230 may remain thin from the glass plate 104 to a distance of about 300 microns into the sample placed atop the glass sheet 104. Additionally, oil layer 112 prevents an air gap from forming between glass plate 104 and the wavefront- and index-matching element 212. Such an air gap may cause a refractive mismatch between the wavefront- and index-matching element 212 and the air, resulting in optical aberrations. As such, oil layer 112 may directly contact a surface of the wavefront- and index-matching element 212 and a lower surface of glass plate 104. As previously described, the wavefront- and index-matching element 212 may comprise a curved surface that is well-matched with the illumination 202 and collection 204 wave fronts as they transition from air into glass (or vice versa). In addition, the wavefront- and index-matching element 212, oil layer 112, and glass plate 104 are all precisely index-matched (e.g., n=1.464 within a tolerance of +/−0.01), and, unlike the water-filled prism, the oil layer 112 does not require refilling. Further, in at least some examples, the sample 206 may be soaked and/or covered in the oil of oil layer 112 or in another liquid in order to index-match the sample 206 to the various other layers.

Figure 2:
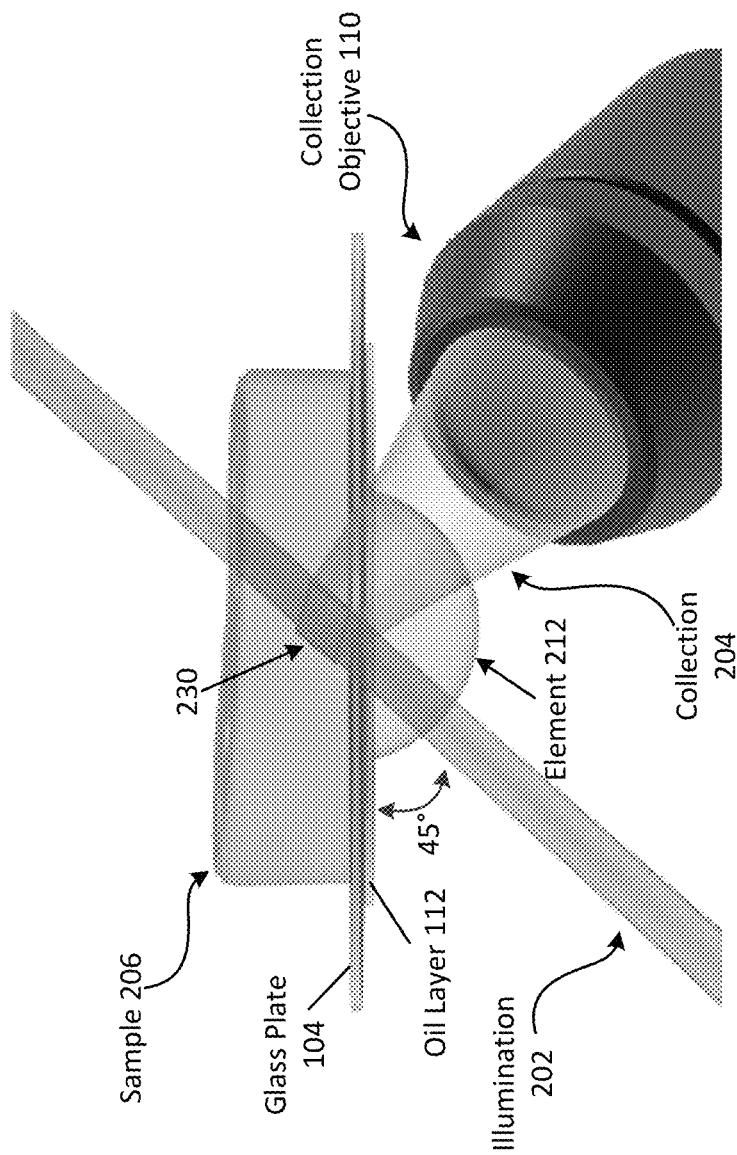
FIG. 2 illustrates an example view of a light sheet microscope including a solid-immersion lens, in accordance with various embodiments of the present disclosure.

The illumination 202 depicted in FIG. 2 may generate a Gaussian-profile illumination light sheet 230 within the sample 206 with a beam waist, $\omega_0$ ~6 μm, (NA 0.03) using, for example, a cylindrical lens. Fluorescence from the sample 206 may be collected by a collection objective 110, (e.g., 4×NA=0.28), oriented perpendicular to the plane of illumination light sheet 230. In some examples, this combination of illumination and collection NA provides sufficient contrast (signal-to-background ratio, SBR) to image most fresh uncleared tissues down to a depth of ~50 μm, with subcellular lateral resolution of ~2.0 μm or better (depending upon the optics used). Additionally, the combination of illumination and collection NA may provide sufficient contrast to image cleared tissues or other samples to a depth of about 500 μm or more. In various examples, images of the illuminated portions of the sample 206 may be collected by a high-speed sCMOS camera with a sampling density of ~1 μm/pixel (Nyquist sampling for a system with 2-μm resolution). The LSM device 102 depicted in FIG. 2 may be capable of achieving near-diffraction-limited performance across the entire field of view. The illumination and collection beams may be oriented at an approximately 45° angle with respect to the glass plate 104. Accordingly, there may be an angle of approximately 90° (e.g., +/−2%) between an optical path of the collection beam and an optical path of the illumination beam. In other implementations, the illumination and collection beams may be oriented at angles that are not at a 45° angle with respect to the glass plate (e.g. 60° and 30°, respectively), but are oriented at an angle of 90° with respect to each other.

Figure 3:
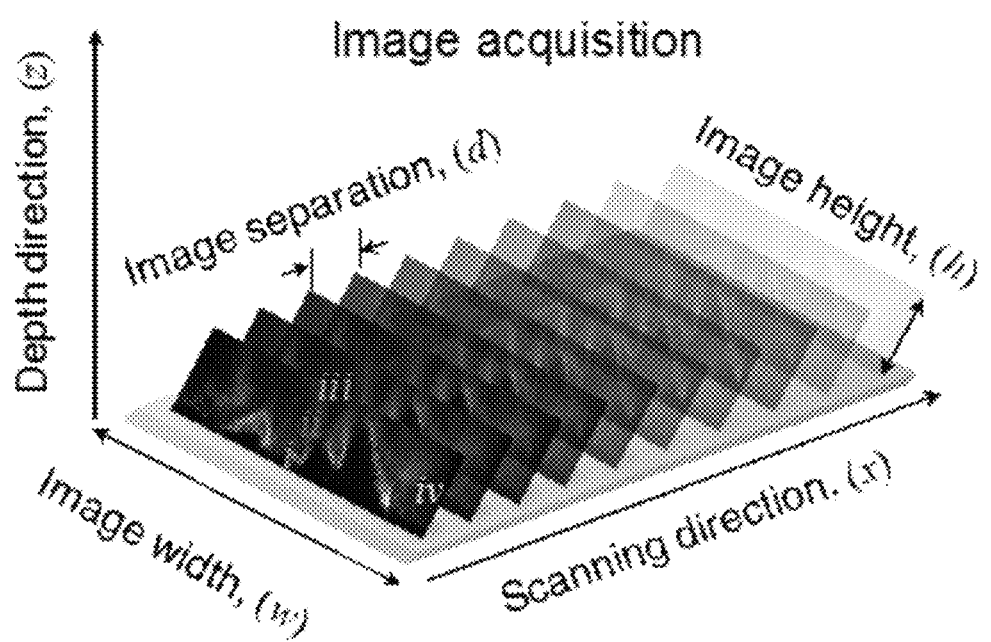
FIG. 3 depicts a geometry of imaged light sheets captured by a light sheet microscope, in accordance with various embodiments of the present disclosure.

The geometry of the imaged light sheets within the tissue sample is shown in FIG. 3. The images are collected at an oblique 45° angle with an image width, w, image separation, d, and image height, h. The image width is limited by the objective lens, which may, in some examples, have a field of view of ~2 mm in diameter. In other examples, different diameter objective lenses may be used, in accordance with various other embodiments. The distance between images along the scan dimension (x dimension) may be d=1.2 μm in some examples. Various sampling pitches in the x dimension may be selected, as desired. Finally, the image height may be chosen to be 256 vertical camera pixels (corresponding to h ~300 μm inside the tissue sample 206), which may provide an optimal trade-off between camera frame rate (imaging speed) and the axial field of view (critical to fully image the tissue-surface irregularities). In various examples, the imaging rate may be increased by capturing fewer pixels along the image-height direction, h. Increasing the imaging rate may be useful for tissues that are able to lay flatter against the glass plate 104, as the surface irregularities of such samples may extend over a shorter range of distances with respect to the surface of the glass plate 104.

Motorized stage 106 may be used to acquire image strips (e.g., width=2 mm) in succession to cover the entire surface of the sample 206. In various examples, the maximum size may be limited by the optics and/or by the size of the motorized stage. In some examples, the maximum size may be about 10×10 cm, although the maximum size may be made larger or smaller using different objectives and motorized stages. With a sampling pitch of 1.2 μm/pixel and 2048 (w)×256 (h) pixel image size, the LSM device 102 may be able to image tissue samples at a speed of ~48 sec/cm$^2$, resulting in 3D datasets with ~40 GB/cm$^2$. The resulting LSM images may be flat-field corrected to compensate for vignetting (for a <10% intensity variation across each raw image), sheared to account for the oblique orientation in the sample, and stitched together to form a volumetric mosaic with 256 pixels in the axial (depth) dimension. To image the surface of an irregular tissue, an extended-depth-of-focus (EDF) algorithm may be utilized. In various examples, the 3D image datasets may be compressed to a resolution-tiled format for real-time viewing using a web-browser. In some examples, the various image processing techniques described above may be performed by at least one processor of a computing device configured in communication with the image sensor of the light sheet microscope system.

Light-Sheet Measurement

Figure 4A:
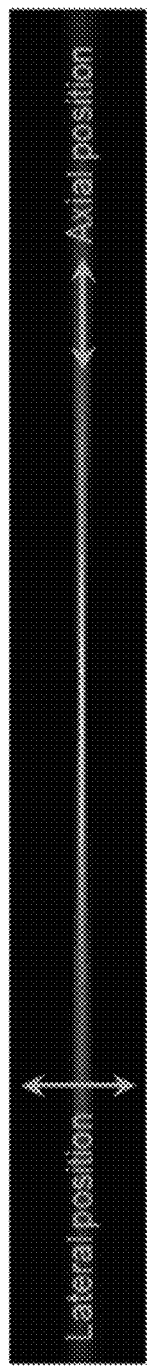
FIG. 4A depicts a representative side-view image of a light sheet produced using a light sheet microscope designed in accordance with various embodiments of the present disclosure.
Figure 4C:
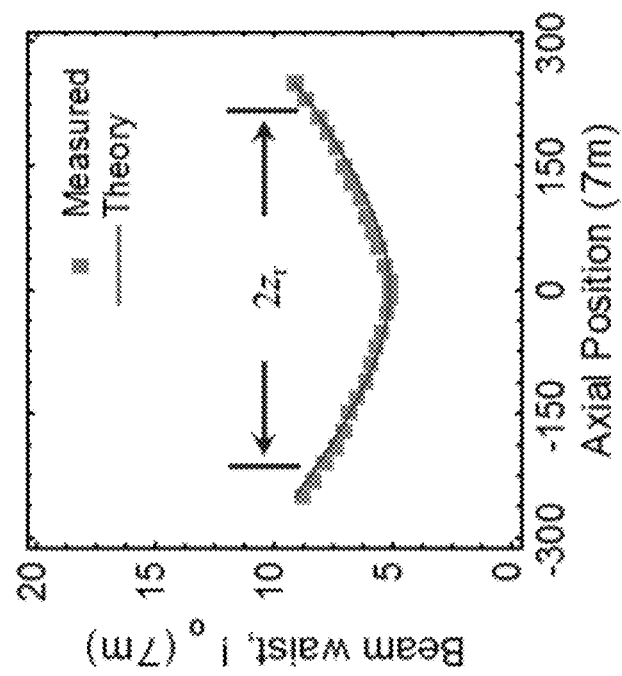
FIG. 4C depicts the measured beam waist as a function of axial position along the light propagation direction of a light sheet produced using a light sheet microscope designed in accordance with various aspects of the present invention.
Figure 4B:
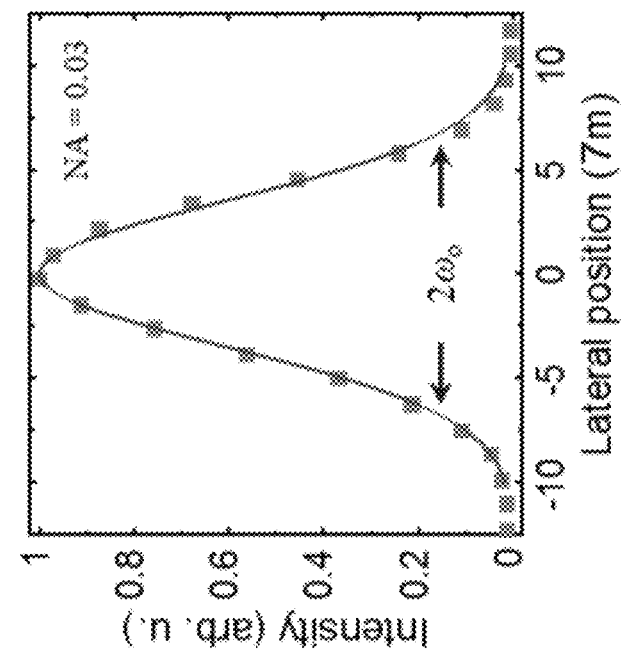
FIG. 4B depicts a plotted line profile of the light sheet from FIG. 4A, in accordance with various embodiments of the present disclosure.

In an example characterization of the Gaussian illumination light sheet, a drop of diluted acridine orange solution (1 mM) may be placed on the sample stage (e.g., on glass plate 104). The illumination cylindrical lens of the illumination objective may be rotated by 90 degrees so that the collection objective 110 may image the side (e.g., the x-z plane). A representative side-view image of the light sheet is shown in FIG. 4A. A line profile in the lateral direction across the center of the beam is plotted in FIG. 4B and fit to a Gaussian profile. The measured beam waist, $\omega_0$, as a function of the axial position along the light propagation direction is shown in FIG. 4C, in comparison to Gaussian beam theory for an illumination NA of 0.03. The measured beam waist is ~6 μm, with a Rayleigh range of $z_R$ ~200 μm. Accordingly, agreement between experimental measurements using LSM device 102 and Gaussian beam theory is shown.

Lateral and Axial Resolution

Figure 5:
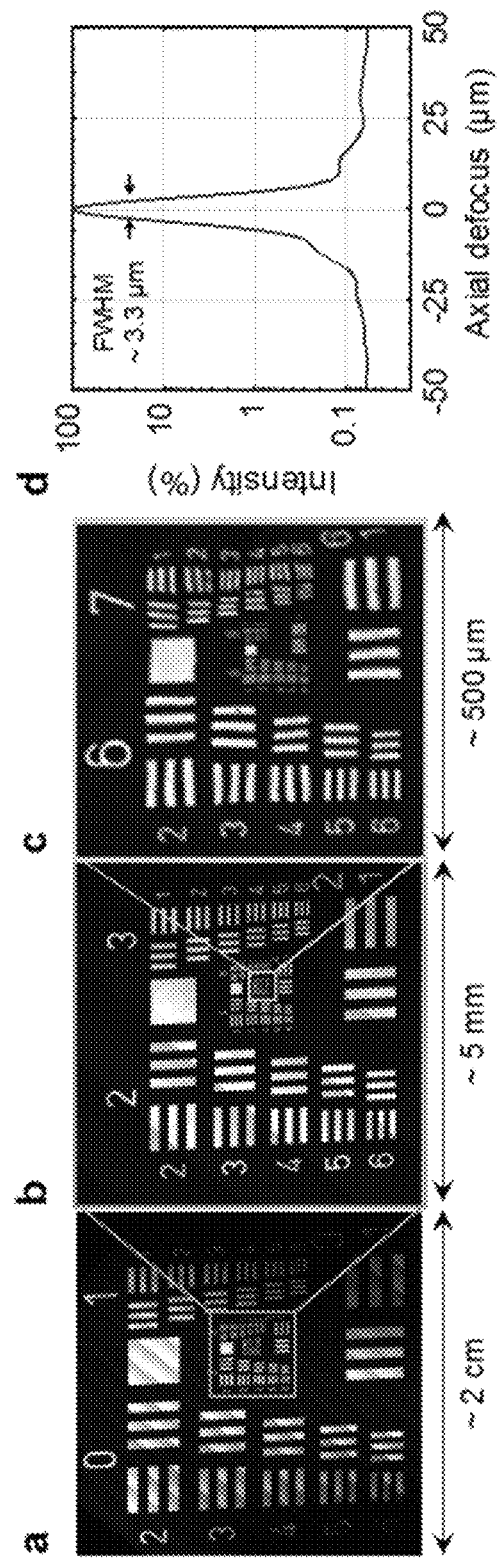
FIG. 5 depicts an example showing lateral resolution of a light sheet microscope designed in accordance with the various techniques described herein.

In an example characterization of the lateral resolution of LSM device 102, a reflectance image of a USAF target (Thorlabs, Newton, N.J.) was acquired and is shown in FIGS. 5a-c at various levels of magnification. As depicted in FIG. 5c, the smallest resolvable lines correspond to Group 8 Element 1, for which the line width is 1.95 μm. Similarly, the axial response to a flat mirror was measured and is plotted in FIG. 5d on a log scale, showing a FWHM "optical-sectioning thickness" of 3.3 μm.

Imaging Fresh Tissues

Figure 6:
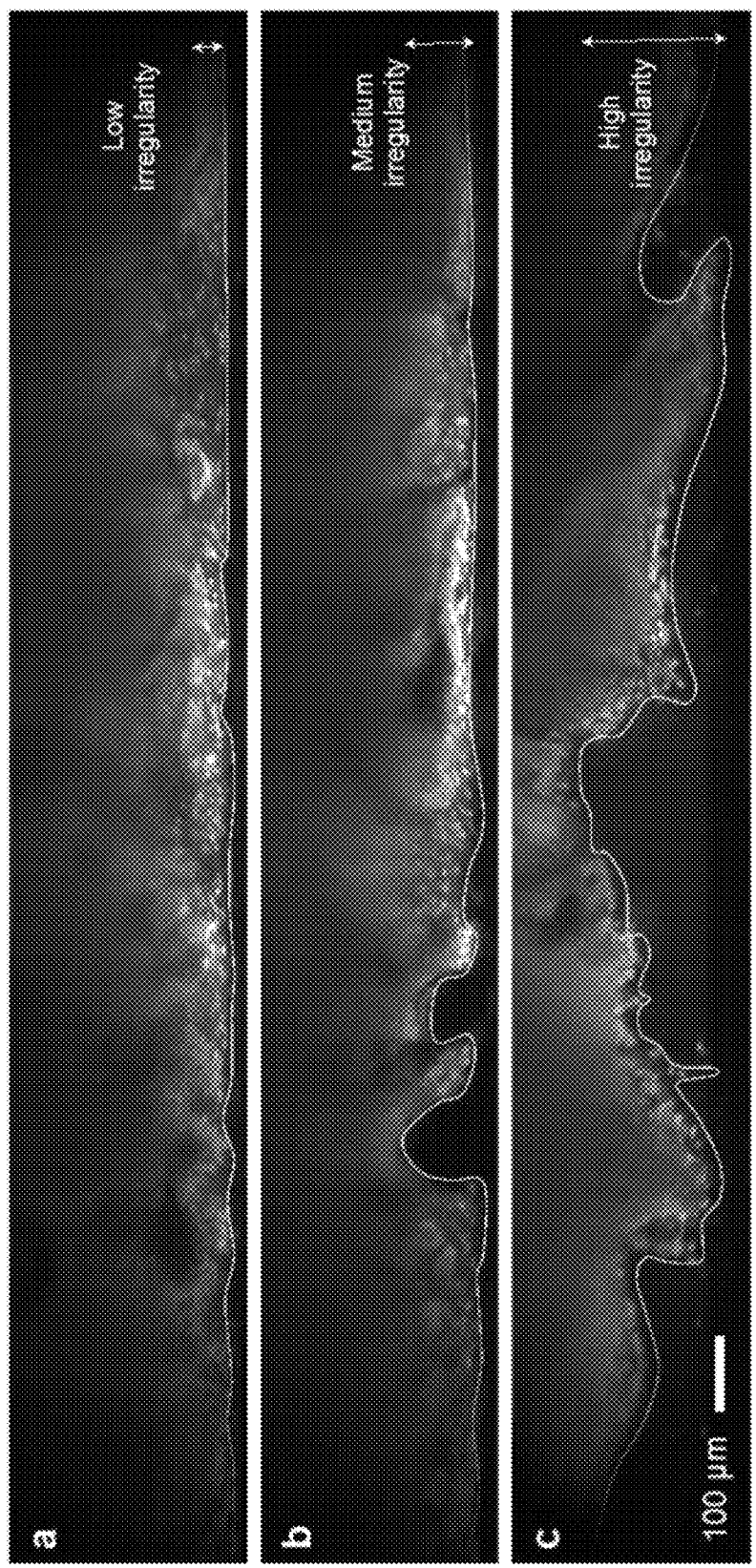
FIG. 6 depicts an example demonstration of an ability of a light sheet microscope, designed in accordance with the present disclosure, to capture images of the irregular surface of freshly cut tissues.

FIG. 6 depicts an example demonstration of an ability of an LSM device 102, designed in accordance with the present disclosure, to capture images of the irregular surface of freshly cut tissues. In the example depicted in FIG. 6, images were acquired from the tongue and kidney of a euthanized mouse. The fresh mouse tissues imaged in FIG. 6 were stained in a 1 mM solution of acridine orange for 20 seconds, rinsed in phosphate-buffered solution (PBS) for 10 seconds, and immediately placed on the glass window of the LSM system for imaging. Representative raw camera images depicting varying degrees of surface irregularity (low, 5-10 μm, medium, 50-100 μm, and high, 200-300 μm) from the mouse kidney are shown in FIG. 6.

Figure 7:
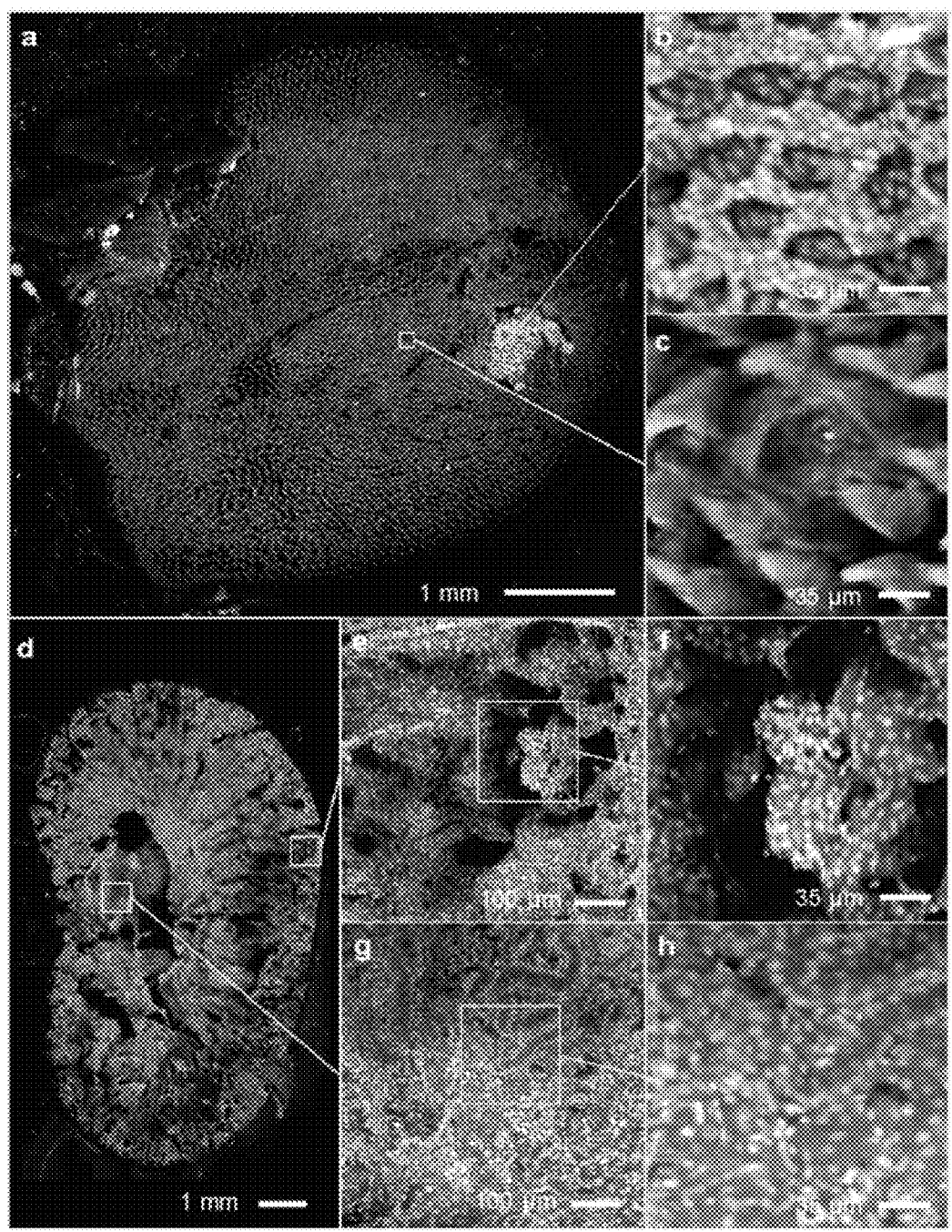
FIG. 7 depicts image mosaics of an extracted mouse tongue and kidney tissue surface imaged using a light sheet microscope designed in accordance with the various techniques described herein.

FIG. 7 depicts the resulting image mosaics of the entire extracted tongue and kidney tissue surface. In FIGS. 7a and 7d respectively, LSM device 102 images are shown of the surface of a freshly excised mouse tongue and the surface of a kidney cross section. Representative zoom-in views depicting the high-resolution capability of the LSM device 102 are shown in FIGS. 7b, 7c, 7e and 7g for the tongue and kidney tissue. FIGS. 7g and 7h show images at higher degrees of zoom for the mouse kidney depicting individual nuclei.

In various examples, LSM device 102 can be used to image the surfaces of fresh tissue specimens at high speed (<1 min/cm$^2$) over a wide-area (up to 10×10 cm) with high resolution (~2 μm) and contrast (a usable imaging depth of ~50 μm) for use in surgical pathology applications (e.g. intra-operative guidance for resection or biopsy procedures, as well as for triaging of post-operative pathology specimens).

In comparison to previous single-axis microscopy systems, the LSM device 102 utilizes separate illumination and collection beam paths, which provide more degrees of freedom to enable three dimensional microscopy with high resolution and a large depth of focus to enable the imaging of fresh tissues with surface irregularities without the need for elaborate tissue-flattening and alignment procedures. By providing simple and fast imaging of fresh tissue samples in a practical timeframe, the LSM device 102 may overcome various logistical and performance issues that have limited the clinical adoption of prior systems.

In some examples, the depth of focus of LSM device 102 can be increased using propagation-invariant illumination beams (e.g., Bessel or Airy beams). LSM device 102 may be operated using wide-field collection, structured-illumination, and/or confocal-line detection. In various examples, confocal-line detection and structured-illumination may improve image contrast. For confocal line detection, a light sheet may be generated rapidly over time by scanning a low-NA point-focused beam, and may be used in conjunction with rolling-shutter sCMOS detection (essentially a confocal slit that moves across the detector plane). In various examples using confocal-line detection, the usable imaging depth in fresh tissues ($\mu_s$ ~10 $mm^{-1}$) can be extended from ~50 μm to ~150 μm. Additionally, in some examples, the resolution of the system can be improved by measuring and deconvolving the 3D point spread function of the system. Finally, as shown in Table 1, the imaging speed may be dependent upon and limited by the read out image size or frame rate of the sCMOS camera detector. Therefore, the speed of LSM device 102 is highly flexible and can be adjusted by modifying the read-out image size (at the expense of imaging depth), or improved in the future using faster cameras as such cameras are developed.

In the context of rapid pathology, the development of a multi-channel LSM device 102 may be of significant diagnostic value. For example, DRAQ5 or DAPI (nuclear) and Eosin (cytoplasmic) have been demonstrated previously as fluorescent analogues to H&E staining. These 'digital-staining' techniques have been shown to improve the diagnostic potential of previous rapid pathology microscopy systems. With ongoing advancements in tissue-clearing techniques, the volumetric information obtained by LSM device 102 may enable new directions for pathology research into the 3D structure of cancers. Finally, obtaining captured images over large, fresh, intact tissue specimens without the need for cutting into conventional pathology cassettes (analogous to the current prohibitively expensive whole-mount pathology slides) may be clinically advantageous.

The volumetric imaging data from the LSM device 102 may result in extremely large imaging datasets. In various examples, the size of the datasets scales may be from about 10-40 $GB/cm^2$ or larger. In various examples, the current image processing may be performed using MATLAB (Mathworks, Natick, Mass.). However, the processing workflow and speed may be improved using a different computational framework (e.g., C++).

In various examples, the LSM device 102 may be described as "inverted" as the illumination objective and collection objective 110 are disposed underneath the glass plate 104 (e.g., the sample stage). The LSM device 102 may be capable of imaging fresh tissues at high speed (<1 min/cm2) over a wide-area (up to 10×10 cm) with high resolution (~2 μm) and contrast (a usable imaging depth of ~50 μm). In comparison to previous systems, the LSM device 102 may provide a long depth of focus (e.g., approximately 300 μm or between 1 μm and 1000 μm) for capturing the irregular surface of fresh tissues without the need for elaborate tissue-flattening or system alignment. The LSM device 102 may provide an optimal balance of imaging speed, resolution, contrast, and ease of use, and has the potential to be a powerful tool for a number of clinical and investigational applications.

Figure 8:
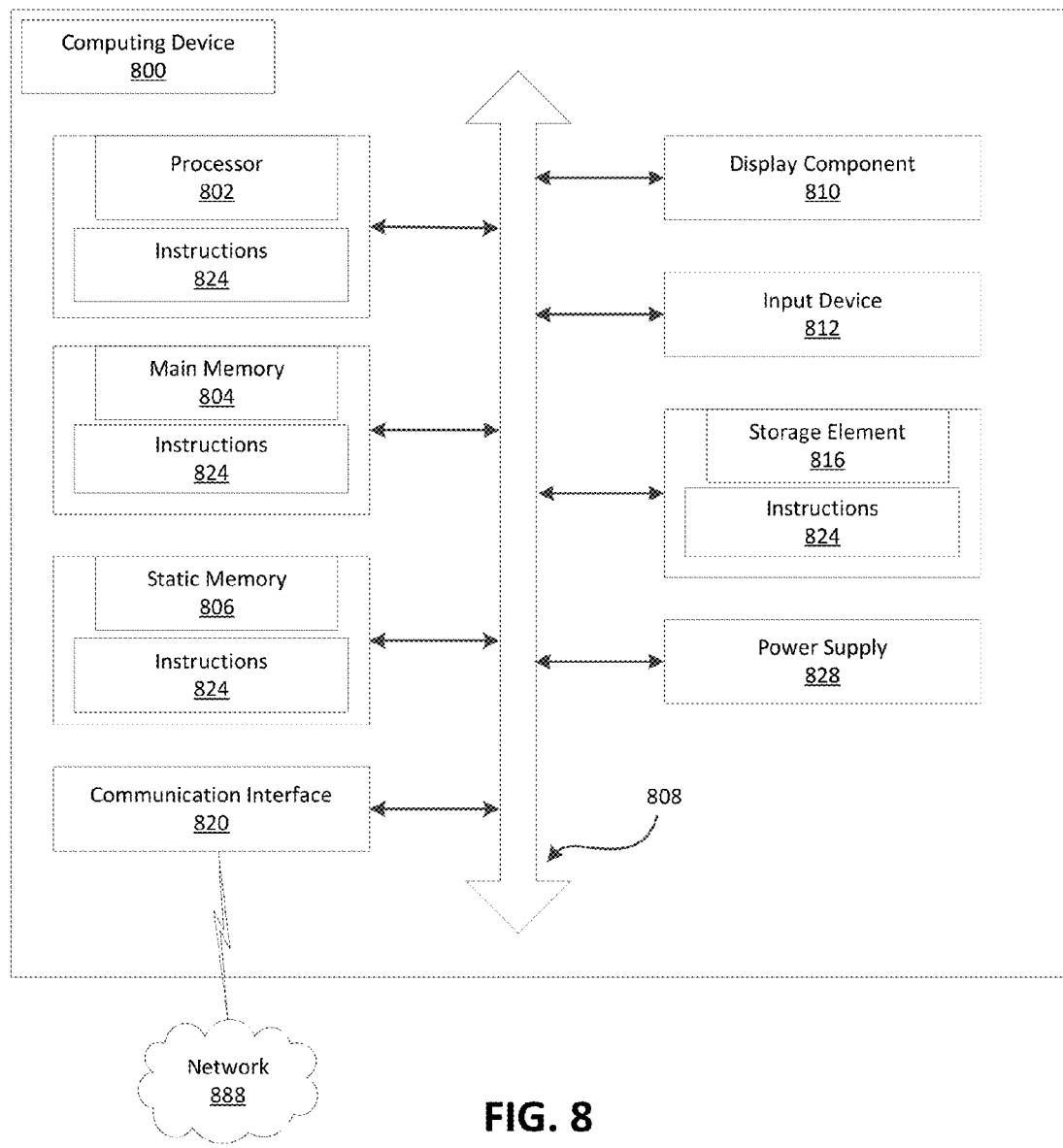
FIG. 8 depicts components of a computing device configured to perform one or more of the methodologies described herein for use with a light sheet microscope designed in accordance with the various techniques described herein.

Referring to FIG. 8, the block diagram illustrates components of a computing device 800, according to some example embodiments, able to read instructions 824 from a non-transitory computer-readable storage medium (e.g., a hard drive storage system) and perform any one or more of the methodologies discussed herein, in whole or in part. Specifically, FIG. 8 shows the computing device 800 in the example form of a computer system within which the instructions 824 (e.g., software, a program, an application, an applet, an app, or other executable code) for causing the computing device 800 to perform any one or more of the methodologies discussed herein may be executed, in whole or in part. For example, the computing device 800 may be used to assemble the mosaic images from the light sheet images depicted in FIG. 3.

In alternative embodiments, the computing device 800 operates as a standalone device or may be connected (e.g., networked) to other computing devices. In a networked deployment, the computing device 800 may operate in the capacity of a server computing device or a client computing device in a server-client network environment, or as a peer computing device in a distributed (e.g., peer-to-peer) network environment. The computing device 800 may include hardware, software, or combinations thereof, and may, as example, be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any computing device capable of executing the instructions 824, sequentially or otherwise, that specify actions to be taken by that computing device. Further, while only a single computing device 800 is illustrated, the term "computing device" shall also be taken to include any collection of computing devices that individually or jointly execute the instructions 824 to perform all or part of any one or more of the methodologies discussed herein.

The computing device 800 includes a processor 802 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 804, and a static memory 806, which are configured to communicate with each other via a bus 808. The processor 802 may contain microcircuits that are configurable, temporarily or permanently, by some or all of the instructions 824 such that the processor 802 is configurable to perform any one or more of the methodologies described herein, in whole or in part. For example, a set of one or more microcircuits of the processor 802 may be configurable to execute one or more modules (e.g., software modules) described herein.

The computing device 800 may further include a display component 810. The display component 810 may comprise, for example, one or more devices such as cathode ray tubes (CRTs), liquid crystal display (LCD) screens, gas plasma-based flat panel displays, LCD projectors, or other types of display devices.

The computing device 800 may include one or more input devices 812 operable to receive inputs from a user. The input devices 812 can include, for example, a push button, touch pad, touch screen, wheel, joystick, keyboard, mouse, trackball, keypad, accelerometer, light gun, game controller, or any other such device or element whereby a user can provide inputs to the computing device 800. These input devices 812 may be physically incorporated into the computing device 800 or operably coupled to the computing device 800 via wired or wireless interface. For computing devices with touchscreen displays, the input devices 812 can include a touch sensor that operates in conjunction with the display component 810 to permit users to interact with the image displayed by the display component 810 using touch inputs (e.g., with a finger or stylus).

The computing device 800 may also include at least one communication interface 820, comprising one or more wireless components operable to communicate with one or more separate devices within a communication range of the particular wireless protocol. The wireless protocol can be any appropriate protocol used to enable devices to communicate wirelessly, such as Bluetooth, cellular, IEEE 802.11, or infrared communications protocols, such as an IrDA-compliant protocol. It should be understood that the communication interface 820 may also or alternatively comprise one or more wired communications interfaces for coupling and communicating with other devices.

The computing device 800 may also include a power supply 828, such as, for example, a rechargeable battery operable to be recharged through conventional plug-in approaches or through other approaches, such as capacitive charging. Alternatively, the power supply 828 may comprise a power supply unit which converts AC power from the power grid to regulated DC power for the internal components of the device 800.

The computing device 800 may also include a storage element 816. The storage element 816 includes the computer-readable medium on which are stored the instructions 824 embodying any one or more of the methodologies or functions described herein. The instructions 824 may also reside, completely or at least partially, within the main memory 804, within the processor 802 (e.g., within the processor's cache memory), or both, before or during execution thereof by the computing device 800. The instructions 824 may also reside in the static memory 806.

Accordingly, the main memory 804 and the processor 802 may also be considered computer-readable media (e.g., tangible and non-transitory computer-readable media). The instructions 824 may be transmitted or received over a network 888 via the communication interface 820. For example, the communication interface 820 may communicate the instructions 824 using any one or more transfer protocols (e.g., HTTP).

The computing device 800 may be implemented as any of a number of electronic devices, such as a tablet computing device, a smartphone, a media player, a portable gaming device, a portable digital assistant, a laptop computer, or a desktop computer. In some example embodiments, the computing device 800 may have one or more additional input components (e.g., sensors or gauges) (not shown). Examples of such input components include an image input component (e.g., one or more cameras), an audio input component (e.g., a microphone), a direction input component (e.g., a compass), a location input component (e.g., a GPS receiver), an orientation component (e.g., a gyroscope), a motion detection component (e.g., one or more accelerometers), an altitude detection component (e.g., an altimeter), and a gas detection component (e.g., a gas sensor). Inputs harvested by any one or more of these input components may be accessible and available for use by any of the modules described herein.

As used herein, the term "memory" refers to a non-transitory computer-readable medium capable of storing data temporarily or permanently and may be taken to include, but not be limited to, random-access memory (RAM), read-only memory (ROM), buffer memory, flash memory, and cache memory. The computer-readable medium is non-transitory in that it does not embody a propagating signal. While the computer-readable medium is described in example embodiments as a single medium, the term "computer-readable medium" should be taken to include any medium, or combination of multiple media, that is capable of storing the instructions 824 for execution by the computing device 800, such that the instructions 824, when executed by one or more processors of the computing device 800 (e.g., processor 802), cause the computing device 800 to perform any one or more of the methodologies described herein, in whole or in part. Accordingly, a "computer-readable medium" refers to a single storage apparatus or device as well as cloud-based storage systems or storage networks that include multiple storage apparatus or devices. The term "computer-readable medium" shall accordingly be taken to include, but not be limited to, one or more tangible (e.g., non-transitory) data repositories in the form of a solid-state memory, an optical medium, a magnetic medium, or any suitable combination thereof.

Figure 9:
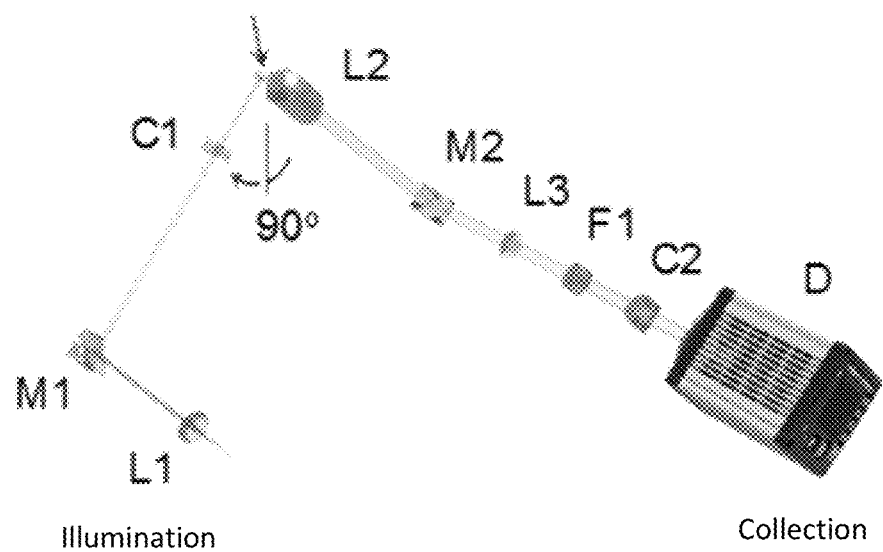
FIG. 9 depicts an example optical schematic of the light sheet microscope, in accordance with various aspects of the present disclosure.

FIG. 9 depicts an example optical schematic of the LSM device 102, in accordance with various aspects of the present disclosure. In the example depicted in FIG. 9, the illumination beam (NA=0.12) is collimated through lens, L1 (f=25 mm), reflected at 45 degrees using M1, and focused into the sample through cylindrical lens, C1 (f=100 mm), resulting in an illumination of NA~0.03. The depicted illumination optics may generate a light sheet which is ~2 mm wide, with a full-width half-maximum (FWHM) thickness of ~6 μm and depth of focus of ~350 μm. The illumination beam may be matched through a custom 15 mm diameter fused-silica wavefront- and index-matching element 212 (as depicted in FIG. 2), a 0.5 mm thick fused-silica matching oil layer (e.g., oil layer 112), and a 1 mm thick 10×10 cm fused-silica flat window (e.g., glass plate 104). The center-thickness of the wavefront- and index-matching element may be reduced from 7.5 mm such that the illumination and collection beams are matched and focused past the oil layer, glass window, and approximately 120 μm into the sample (half of the illumination beam's depth of focus, accounting for the oblique 45-degree illumination angle).

In the example depicted in FIG. 9, fluorescence from the tissue sample may be collected by an objective lens, L2 (e.g., collection objective 110 of FIG. 1, 4×NA=0.28), reflected at 45 degrees from mirror M2, focused through a tube lens, L3 (f=100 mm) through an emission filter, F1, and an additional low-power aberration-correcting cylindrical lens, C2 (f=2000 mm) onto a high-speed sCMOS camera with a 2048×2048 pixel detector or onto some other image sensor. In various examples, captured images may be transferred at maximum data transfer rates to a dedicated workstation comprised of a high-speed RAID0 hard disk using a CameraLink interface or equivalents thereof. In addition to correcting aberrations, the wavefront- and index-matching element may increase the collection NA by the refractive index of fused-silica (n ~1.46) to ~0.19. In addition, the cylindrical lens, C2, may be used to mitigate additional slight astigmatism in the collection optics, which arises due to the mismatch between the fused-silica window (n ~1.46) and fresh tissue (n ~1.38). Finally, in the example depicted in FIG. 9, the collection NA may provide a field of view of ~2 mm, a lateral resolution of ~2.0 μm within the sample, and may be collected by a sCMOS camera with a sampling density of ~1.2 μm/pixel.

Image Processing

After being acquired, the raw LSM image data may undergo a number of image processing steps to render the final images of the sample. Various example image processing steps are described below.

Flat-Field Correction.

Each individual LSM image may be flat-field corrected for variations in the intensity across the Gaussian, vignetting of the objective and tube lens collection optics, inter-pixel variations in the sensitivity of the sCMOS camera, and intrinsic aberrations to the LSM device 102. In various examples, in order to account for the aforementioned effects, prior to imaging, a drop of homogeneous fluorescent-dye staining solution may be imaged to acquire a reference image. Every subsequent raw image may be divided by this reference image to perform flat-field correction.

Shearing.

In various examples, the captured images correspond to oblique 45-degree planes within the sample (e.g., as depicted in FIG. 3). However, in some examples, when being stored digitally, the various images may form a data cube in which the images are oriented at 90 degrees. Accordingly, in post-processing, the images may be sheared by 45 degrees in the x-z plane to create a trapezoidal data volume.

Mosaicking.

In various examples, after being sheared, each image strip may be registered to adjacent image strips using a scale-invariant feature transform (SIFT) image registration algorithm (e.g., in MATLAB or some other programming framework. When scanning, an overlap of 250 µm may be used between adjacent image strips for registration, and a linear blending of each image strip may be used to generate the final image mosaic. This operation may initially be performed for a single en face image mosaic in the x-y plane, and the resulting registration and blending operations may be determined from this single plane and applied to all of the imaging data at each depth, z.

Tissue Surface Extraction.

In the example described above, the imaging data may now represent a 3D volume of multiple registered, blended, and stitched 2D image mosaics as a function of depth in the sample. To further reduce the dimensionality of the data, and extract only the irregular surface of the sample, an extended-depth of field (EDF) algorithm may be used, where a single 2D en face mosaic may be generated by extracting only the "in-focus" portions of each 2D mosaic as a function of depth, z. The EDF algorithm may generate an extended image stack by scanning the microscope focus axially, which may result in de-focusing or blurring for portions of the bright-field images. The LSM device 102 may directly acquire a 3D image stack, which may be entirely in focus. The blurring may instead be a result of light scattering and optical aberrations. However, the net effect of the EDF algorithm is identical, in that the in focus sample surface is extracted.

Resolution-Tiling.

The resulting multi-gigapixel 2D image mosaics from the EDF algorithm (as well as the individual mosaics at each depth in the tissue sample) may be resolution-tiled for real-time viewing and zooming, similar to an online map provider (e.g., similar to panning and zooming in Google Maps).

Viewing.

The tiled data files may be transferred to and stored on a cloud server or other data repository for online-access using a web browser.

FIGS. 10A-10G depict example image processing techniques in accordance with various aspects of the present disclosure. Image data captured by LSM device 102 may initially be captured in a raw image data format. In various examples, prior to the other image processing techniques depicted in FIGS. 10A-10G, the image data may be converted into a different file format as individual images or as a common data format (e.g., HDF5, DICOM) or as compressed files.

Figure 10A:
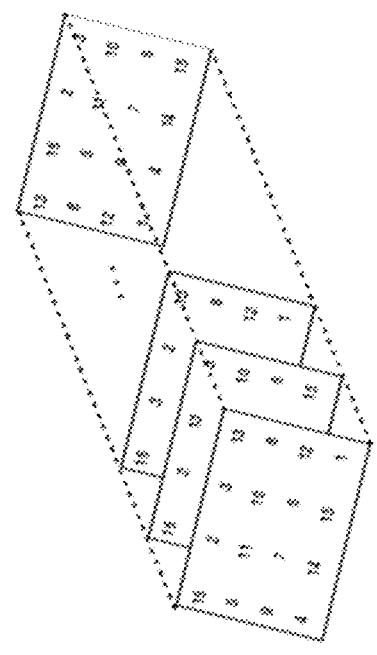
FIGS. 10A-10G depict example image processing techniques in accordance with various aspects of the present disclosure.
Figure 10A:
Figure 10A:
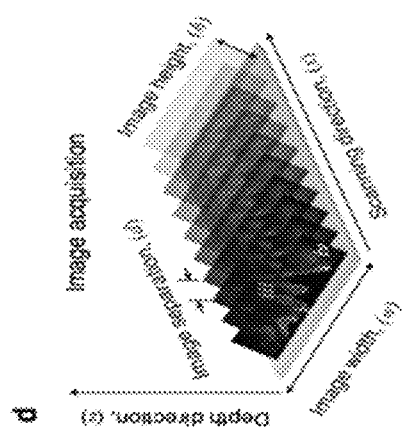
Figure 10B:
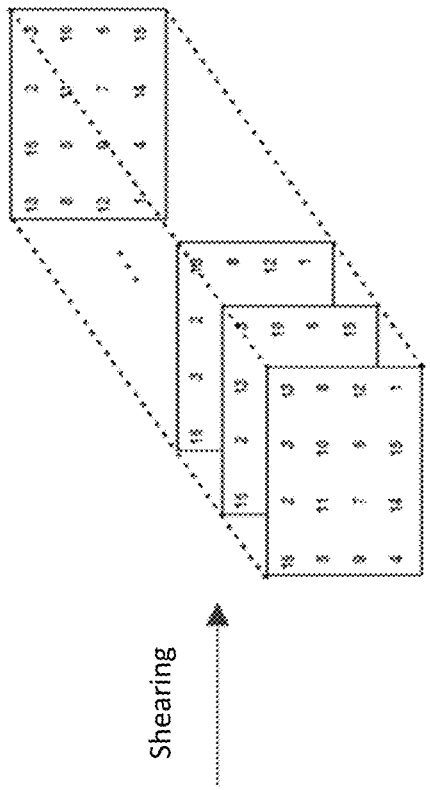
Figure 10B:
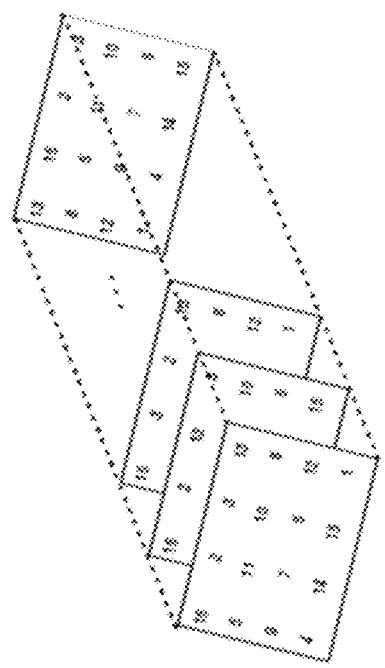

After storing the image data in a desired format, the image data may be read into a 3D array, as illustrated in FIG. 10A. The 3D array may be stored in a memory or as a memmap (e.g., data mapped onto a hard drive). As depicted in FIG. 10A, the 3D array may comprise image data arranged at 45 degrees. As depicted in FIG. 10B, the 3D array may be sheared into a rectangular volume of images.

Figure 10C:
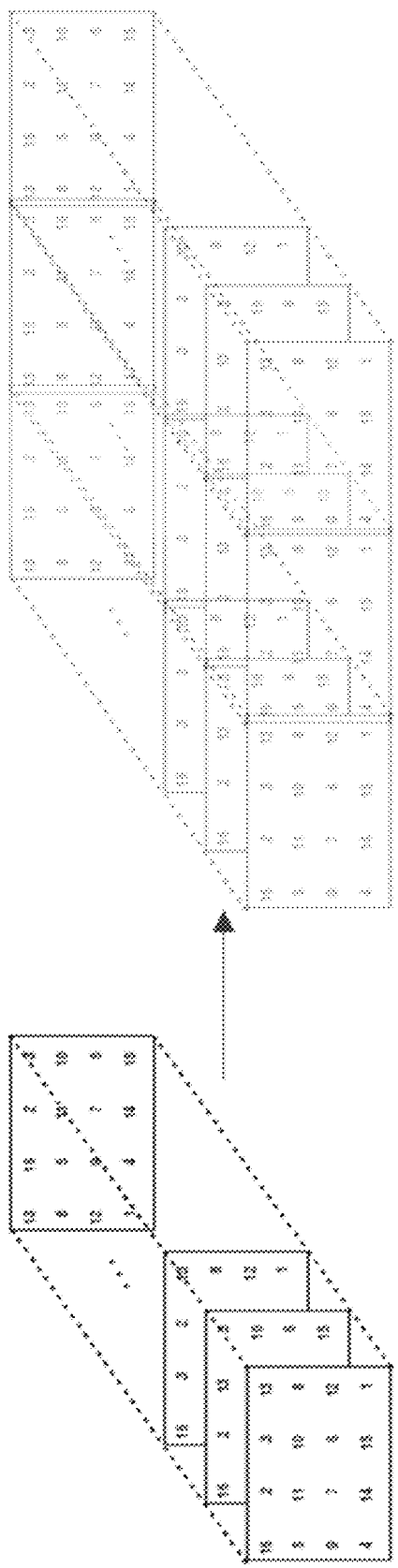
Figure 10D:
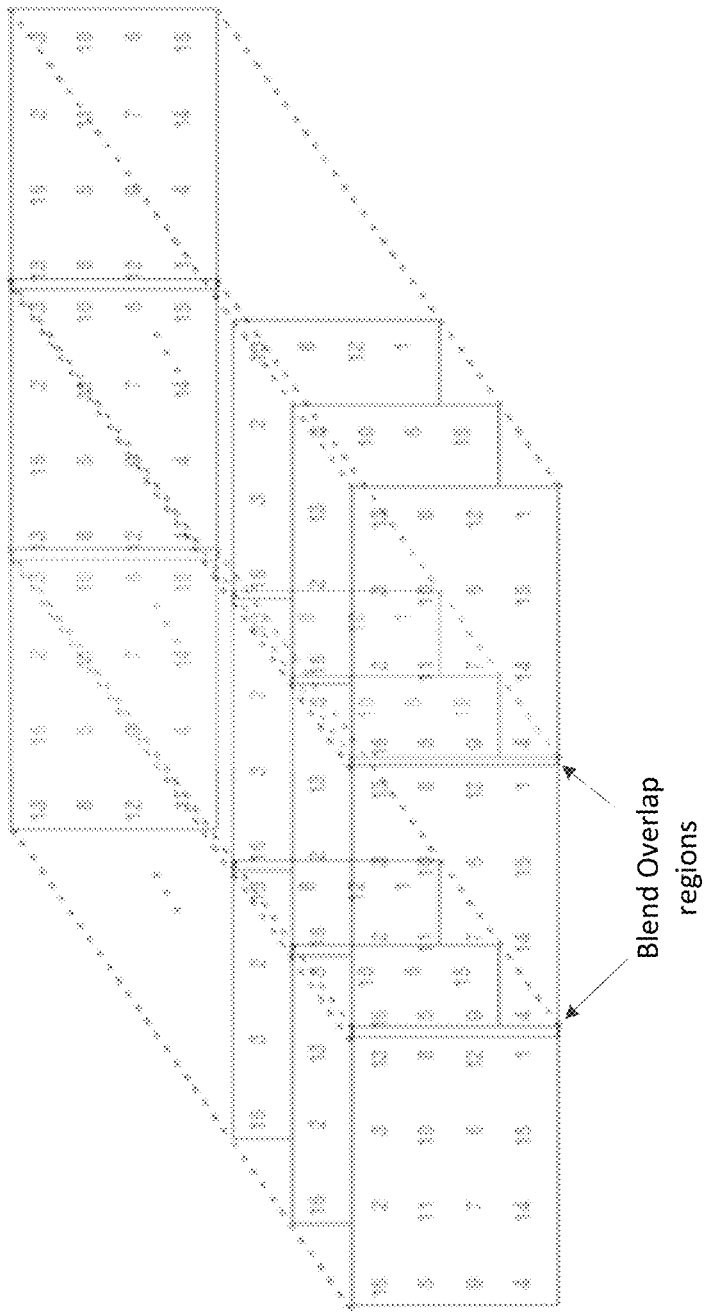

Image data matching algorithms may thereafter be used to match adjacent images in the x-y plane to create a stitched rectangular volume as depicted in FIG. 10C. Overlapping portions of the stitched rectangular volume may be blended using various image filters to generate a seamless, imperceptible stitching of the constituent images of the rectangular volume as depicted in FIG. 10D. Thereafter, periodic irregularities in the images may be filtered using a Fourier transform to generate a stitched, blended 3D array without periodic irregularities.

Figure 10E:
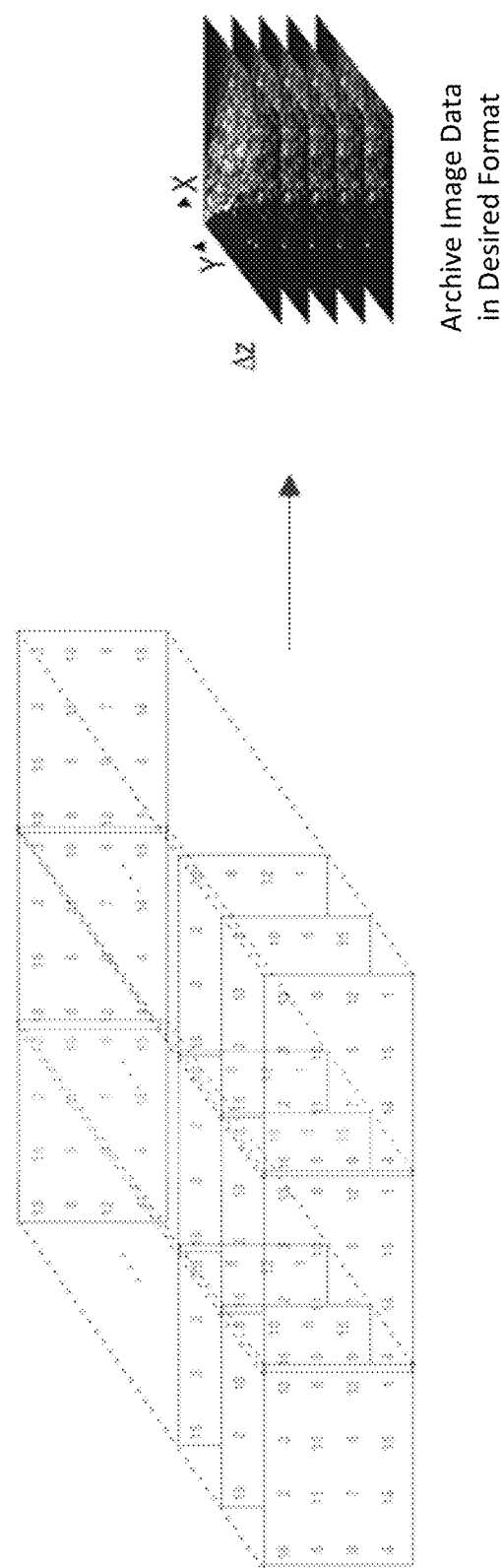

Thereafter, as depicted in FIG. 10E, the stitched images may be archived in a desired image format, representing the entire 3D volume of the imaged sample. In various examples, the stitched images may be stored on one or more remotely accessible data repositories. Additionally, the various image processing techniques described herein may be implemented in a distributed computing environment (e.g., "on the cloud").

Figure 10F:
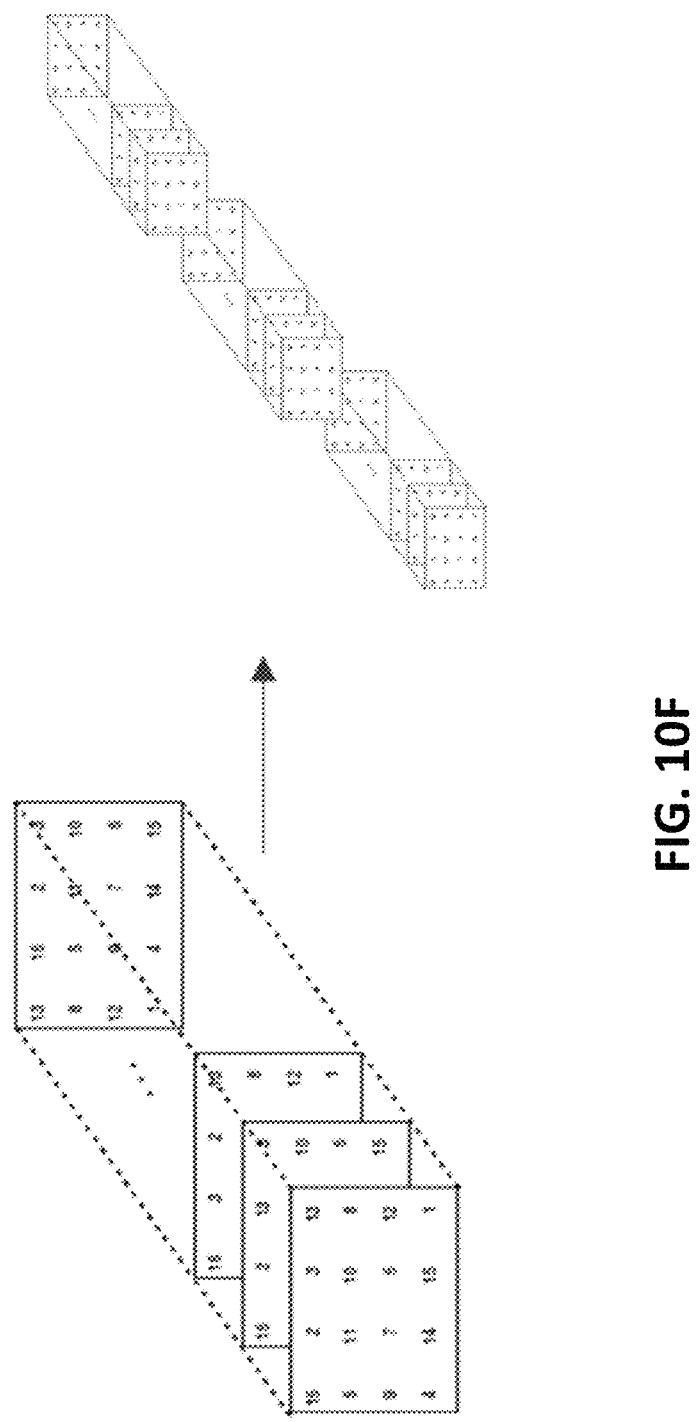
Figure 10G:
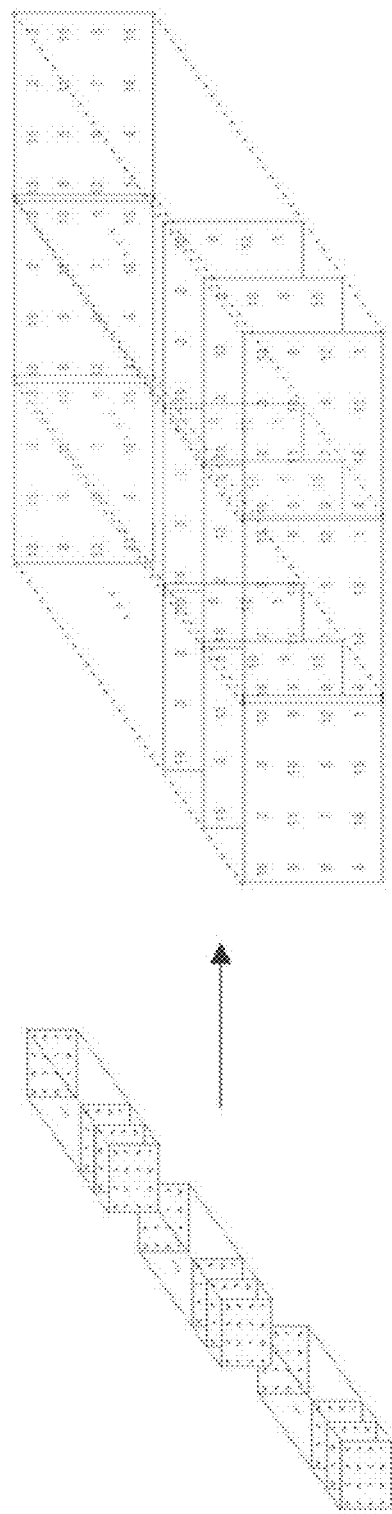

As shown in FIG. 10F, the full image data comprising 3D arrays including image data arranged at 45 degrees may be partitioned into smaller volumes. FIG. 10G depicts an example of parallel processing/stitching whereby the smaller, partitioned volumes generated in FIG. 10F are stitched in parallel to increase speed of the stitching operations described above.

The various image processing techniques described above allow 2D images to be viewed in the x, y, and z planes of any region of the specimen being imaged. Additionally, the various image processing techniques described above allow for viewing of 3D images stored as a hierarchy of 3D volumes with different resolutions to facilitate seamless zooming in and out of the entire specimen. Additionally, the various image processing techniques described above allow for viewing 3D images of segmented structures including glandular lumens, nuclei, vessels, etc.

Further, the LSM device 102 and the image processing techniques described herein may offer several advantages over previous imaging devices and processing techniques, including, but not limited to triaging tissue for downstream analyses including formalin-fixed paraffin embedded sample histology, biobanking, genetic sequencing, flow cytometry, immunohistochemistry, and/or in-situ hybridization. Real-time analysis for intraoperative guidance. Real-time analysis for specimen adequacy during biopsy procedures, including determining whether there is sufficient tumor volume for downstream genetic sequencing or biobanking. Volumetric imaging of cleared samples for the purpose of definitive diagnosis, 3D immunofluorescence and/or in-situ hybridization, 3D microdissection using a precision cutting instrument and/or laser. Additionally, the imaging of small samples placed on the open-top stage (e.g. glass plate 104) may be massively parallelized. For example, multi-well plates containing cell cultures or organoids and/or other customized sample holders containing many specimens may be quickly imaged for analysis.

Figure 11:
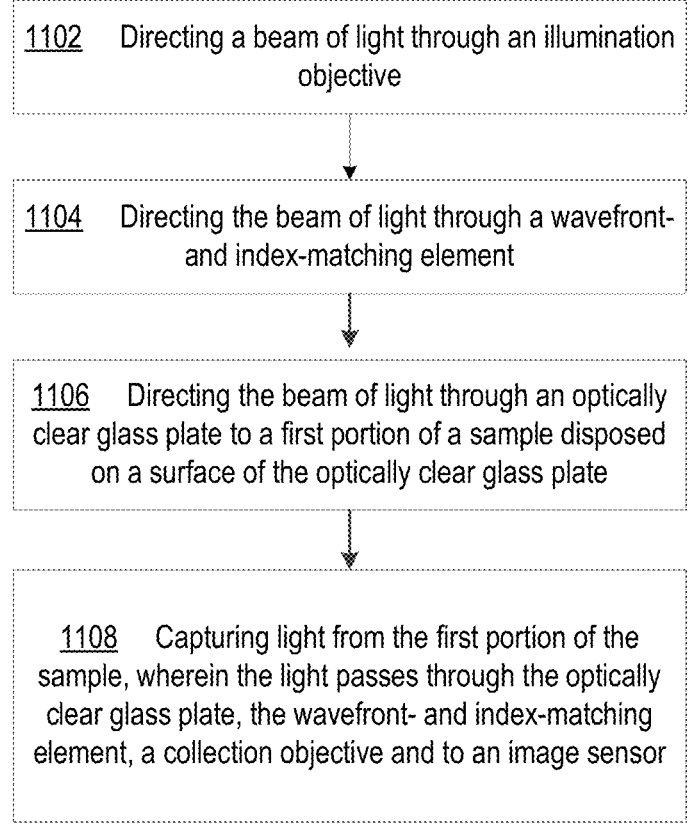
FIG. 11 depicts an example image capture process for a light sheet microscope, in accordance with various aspects of the present disclosure.

FIG. 11 depicts an example image capture process for a light sheet microscope, in accordance with various aspects of the present disclosure.

The process depicted in FIG. 11 may begin at action 1102, "Directing a beam of light through an illumination objective." At action 1102, a beam of light may be directed through an illumination objective comprising one or more lenses. As previously described, the illumination objective may be arranged so as to be optically aligned at a substantially 45° angle with respect to a plane of glass plate 104.

Processing may proceed from action 1102 to action 1104, "Directing the beam of light through a wavefront- and index-matching element." At action 1104, the beam of light emitted from the illumination objective may be directed through a wavefront- and index-matching element (e.g., a solid immersion lens, etc.). As previously described, the wavefront- and index-matching element may be, in some examples, a truncated hemispherical lens. A material of the wavefront- and index-matching element may be precisely index-matched to glass plate 104 and to an oil layer separating the wavefront- and index-matching element from the glass plate 104. In various examples, glass plate 104 may instead be replaced by a non-glass optically clear material, as desired, so long as the material is index matched with the oil and the wavefront- and index-matching element.

Processing may proceed from action 1104 to action 1106, "Directing the beam of light through an optically clear glass plate to a first portion of a sample disposed on a surface of the optically clear glass plate." The light may form a focal plane light sheet illuminating a portion of a sample resting on the glass plate 104. Because of a depth of focus of the focal plane light sheet, the light may be effective to capture images of irregular, non-planar surfaces of the sample in accordance with the image processing techniques described herein.

Processing may proceed from action 1106 to action 1108, "Capturing light from the first portion of the sample, wherein the light passes through the optically clear glass plate, the wavefront- and index-matching element, a collection objective and to an image sensor." At action 1108, the light from the illuminated portion of the sample (e.g., a fluorescent signal and/or reflected light) may be collected by a collection objective and captured by an image sensor (such as the sCMOS image sensors described herein) after passing through the glass plate, the oil layer and the wavefront- and index-matching element. In various examples, the glass plate (and thus the position of the sample) may be translated to capture multiple different images of the sample, as shown in FIG. 3. Thereafter, the multiple images may be stitched together using the various image processing techniques discussed herein to generate a volumetric dataset representing a (potentially) irregular surface of the sample.

While the invention has been described in terms of particular embodiments and illustrative figures, those of ordinary skill in the art will recognize that the invention is not limited to the embodiments or figures described. The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While specific embodiments and examples for the disclosure are described herein for illustrative purposes, various equivalent modifications are possible within the scope of the disclosure, as those skilled in the relevant art will recognize. Such modifications may include, but are not limited to, changes in the dimensions and/or the materials shown in the disclosed embodiments.

Specific elements of any embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A microscope comprising:
   a motorized movable stage comprising an optically transparent plate having a first side for receiving illumination light and a second, parallel, opposing side, the motorized movable stage being operable to move the optically transparent plate;
   an illumination objective disposed adjacent to the first side of the optically transparent plate, the illumination objective comprising illumination optics configured to direct an illumination beam of light along a first optical path towards a sample supported by the second side of the optically transparent plate to illuminate the sample, wherein the first optical path is at a first angle which is oblique to the second side of the optically transparent plate;
   a collection objective disposed adjacent to the first side of the optically transparent plate, the collection objective comprising an objective lens configured to collect light from the sample through the optically transparent plate and to direct the collected light along a second optical path different than the first optical path, wherein the second optical path is at a second angle which is oblique to the second side of the optically transparent plate; and a wavefront- and index-matching element comprising a solid immersion lens disposed on the first side of the optically transparent plate, wherein the optically transparent plate and the wavefront- and index-matching element comprise a first refractive index value, and wherein the wavefront- and index-matching element comprises a curved surface configured to receive the illumination beam of light and direct the illumination beam of light to pass along the first optical path through the wavefront- and index-matching element and through the first side and the second side of the optically transparent plate to form an illumination light sheet illuminating a region of the sample, and wherein the wavefront- and index-matching element is further configured to direct light from the illuminated region of the sample towards the collection objective along the second optical path; and an optical imaging device coupled to receive the light collected by the collection objective to capture optical images of the illuminated region sample, wherein the illuminated region is at an oblique angle to the first side of the optical plate.

2. The microscope of claim 1, wherein the wavefront- and index-matching element comprises a gradient refractive index profile.

3. The microscope of claim 1, wherein an approximately 90° angle exists between the first optical path and the second optical path.

4. The microscope of claim 1, wherein the motorized movable stage is effective to translate along a first axis and a second axis orthogonal to the first axis such that the illumination light sheet passes through different portions of the optically transparent plate.

5. The microscope of claim 1, further comprising an oil layer disposed between the optically transparent plate and the wavefront- and index-matching element, wherein oil in the oil layer is in contact with at least a first portion of the first side of the optically transparent plate and with at least a second portion of the wavefront- and index-matching element.

6. The microscope of claim 5, wherein the oil comprises the first refractive index value.

7. The microscope of claim 1, wherein a depth of focus of the illumination light sheet is between 1 and 1000 μm extending in a direction away from the second side of the optically transparent plate.

8. The microscope of claim 1, wherein the illumination objective, the collection objective and the wavefront- and index-matching element are aligned such that a beam waist of the illumination light sheet is positioned between 1-200 μmicrons above the optically transparent plate.

9. A microscope system comprising:

at least one processor operable to receive image data of different image stripes obtained from different stripes of a sample and to process the received image data to form a processed image representing a three-dimensional image of the sample by combining the different image stripes;

a computer-readable non-transitory memory configured to be in communication with the at least one processor and operable to store data in connection with image processing by the at least one processor;

a motorized movable stage comprising an optically transparent plate having a first side for receiving illumination light and a second side supporting the sample, the second side being opposite, and parallel to, the first side, wherein the motorized movable stage is operable to move the optically transparent plate to different positions for obtaining the different image strips of the sample;

an illumination objective disposed adjacent to the first side of the optically transparent plate, the illumination objective comprising illumination optics configured to direct an illumination beam of light along a first optical path towards the sample to illuminate the sample, wherein the first optical path is at a first angle which is oblique to the second side of the optically transparent plate;

a collection objective disposed adjacent to the first side of the optically transparent plate, the collection objective comprising an objective lens configured to collect light from the sample through the optically transparent plate and to direct the collected light along a second optical path different than the first optical path, wherein the second optical path is at a second angle which is oblique to the second side of the optically transparent plate; and a wavefront- and index-matching element comprising a solid immersion lens disposed on the first side of the optically transparent plate, wherein the illumination beam of light passing through the illumination objective is received by a curved surface of the wavefront- and index-matching element configured to direct the illumination beam of light to pass along the first optical path and through the wavefront- and index-matching element, through the first and the second side of the optically transparent plate, to form an illumination light sheet on the second side of the optically transparent plate to illuminate one strip of the sample within a spatial coverage of the illumination light sheet at one corresponding position of the sample and the optically transparent plate of the different positions set by the motorized movable stage, and wherein the wavefront- and index-matching element is further configured to direct light from the strip towards the collection objective along the second optical path, thus obtaining the image strips obtained from different strips of the sample at the different positions set by the motorized movable stage; and an optical imaging device coupled to receive the light collected by the collection objective to capture the image strips of the sample, wherein the image strips are at an oblique angle to the first side of the optically transparent plate.

10. The microscope system of claim 9, wherein the optical imaging device captures the image strips of the sample with a resolution of between 1-2 μm.

11. The microscope system of claim 9, wherein:
the sample comprises an irregular surface; and
the at least one processor is effective to stitch the image data of different image strips obtained from different stripes of the sample together to form a volumetric dataset that contains the irregular surface of the sample.

12. The microscope system of claim 9, further comprising an oil layer disposed between the optically transparent plate and the wavefront- and index-matching element, wherein oil in the oil layer is in contact with at least a first portion of the first side of the optically transparent plate and with at least a second portion of the wavefront- and index-matching element.

13. The microscope system of claim 12, wherein the oil, the optically transparent plate and the wavefront- and index-matching element are index-matched to a first refractive index value within a tolerance of +/−0.01.

14. The microscope system of claim 9, wherein a depth of focus of the illumination light sheet is between 1 and 1000 µm extending in a direction away from the second side of the optically transparent plate.

15. The microscope system of claim 9, wherein the wavefront- and index-matching element comprises a gradient refractive index profile.

16. A method of capturing an image using a microscope by separating illumination optics from image-capturing optics, the method comprising:
    directing a focused beam of light along a first optical path through an illumination objective, a wavefront- and index-matching element comprising a solid immersion lens, and a first side and second side of an optically transparent plate to a first portion of a sample disposed on a second side of the optically transparent plate wherein the second side is opposite and parallel to the first side and wherein the first optical path and the first illuminated region are at a first angle which is oblique to the second side of the optically transparent plate;
    capturing, by an image sensor positioned adjacent the first side of the optically transparent plate, a light signal from the first portion of the sample, wherein the light signal passes along a second optical path through the second side of the optically transparent plate, the first side of the optically transparent plate, the wavefront- and index-matching element, and a collection objective, wherein the light signal is captured by the image sensor as a first frame of image data, wherein the second optical path is at a second angle which is oblique to the second side of the optically transparent plate, and wherein the first frame of image data is at an oblique angle to the first side of the optically transparent plate.

17. The method of claim 16, further comprising directing the focused beam of light along the first optical path through an oil layer disposed between the first side of the optically transparent plate and the wavefront- and index-matching element, wherein oil of the oil layer, the optically transparent plate, and the wavefront- and index-matching element are index-matched to within a tolerance of +/−0.01.

18. The method of claim 16, further comprising:
    moving the optically transparent plate in a lateral direction parallel to a plane of the optically transparent plate to position a second portion of the sample in the first optical path of the focused beam of light, wherein the focused beam of light is transmitted through the illumination objective, the wavefront- and index-matching element, and the optically transparent plate;
    capturing, by the image sensor, a second light signal from the second portion of the sample, wherein the second light signal is captured as a second frame of image data which is at an oblique angle to the first side of the optically transparent plate; and
    combining the first and second frames of image data to produce a processed image of the first and second portions of the sample with a resolution of between 1-2 µm.

19. The method of claim 18, further comprising:
    stitching, by at least one processor, the first frame of image data and the second frame of image data together to form a volumetric dataset representing an irregular, non-planar surface of the sample.

20. The method of claim 16, wherein an approximately 90° angle exists between the first optical path of the focused beam of light directed through the illumination objective and the second optical path of the light signal passing through the second side of the optically transparent plate, the first side of the optically transparent plate, the wavefront- and index-matching element, and the collection objective.

* * * * *